(12) United States Patent
Kwan et al.

(10) Patent No.: US 7,297,490 B2
(45) Date of Patent: Nov. 20, 2007

(54) AUTHENTICATION OF BIOLOGIC MATERIALS USING DNA-DNA HYBRIDIZATION ON A SOLID SUPPORT

(75) Inventors: Hoi Shan Kwan, Yuen Long (HK); Chun Yin Mak, Hong Kong (CN); Oi Wah Lau, deceased, late of Hong Kong (CN); by Ping Kay Hon, legal representative, Hong Kong (CN)

(73) Assignee: Chinese University of Hong Kong, Hong Kong SAR (CN)

( * ) Notice: Subject to any disclaimer, the term of this patent is extended or adjusted under 35 U.S.C. 154(b) by 307 days.

(21) Appl. No.: 10/797,668

(22) Filed: Mar. 10, 2004

(65) Prior Publication Data

US 2004/0235021 A1    Nov. 25, 2004

Related U.S. Application Data

(60) Provisional application No. 60/453,842, filed on Mar. 10, 2003.

(51) Int. Cl.
*C07H 21/04*    (2006.01)
*C12Q 1/68*     (2006.01)

(52) U.S. Cl. .................... 435/6; 435/91.1; 435/91.2; 536/23.1; 536/24.3

(58) Field of Classification Search .............. None
See application file for complete search history.

(56) References Cited

U.S. PATENT DOCUMENTS

| | | | | |
|---|---|---|---|---|
| 5,874,221 | A * | 2/1999 | Tooley et al. | 435/6 |
| 6,309,840 | B1 * | 10/2001 | Wang et al. | 435/6 |
| 6,541,624 | B1 * | 4/2003 | Singh et al. | 536/24.3 |
| 6,599,701 | B1 * | 7/2003 | Honeycutt et al. | 435/6 |
| 2002/0172945 | A1 * | 11/2002 | Carroll | 435/6 |

* cited by examiner

*Primary Examiner*—Jeanine A. Goldberg
(74) *Attorney, Agent, or Firm*—Occhiuti Rohlicek & Tsao LLP

(57) ABSTRACT

Provided are a method for preparing an array for authenticating biological samples and a method for authenticating the biological samples based on analysis of variable sequences of ribosomal RNA genes as well as a kit for authentication of the biological samples. The hybridization of probes of the samples to the array of overlapping fragments of authentic variable ribosomal RNA gene regions is quantified. The test enables distinction of species or prokaryotic strains and is unaffected by intra-species or strain polymorphism. The method disclosed is illustrated by authentication of traditional Chinese medicinal materials.

28 Claims, 3 Drawing Sheets

AUTHENTICATION OF BIOLOGIC MATERIALS USING DNA-DNA HYBRIDIZATION ON A SOLID SUPPORT

CROSS REFERENCE OF RELATED APPLICATIONS

The present application claims the benefit of U.S. provisional application Ser. No. 60/453,842 filed on Mar. 10, 2003, entitled the same, which is explicitly incorporated herein by reference in its entirety.

BACKGROUND OF THE INVENTION

1. Technical Field of the Invention

The present invention is directed to identification of the source of biologic specimens such as medicinal materials, particularly to a method of determining the identity of plants used in the medicinal materials and a kit used for the identification. The invention is exemplified by methods and kits for differential identification of materials derived from one of three different species of *Ilex*.

2. Description of the Related Art

An effective method of authentication of traditional Chinese medicinal materials is necessary for the development of the industry, as it provides the necessary protection for consumers, minimizes unfair business competition, and prevents health hazards due to materials that adulterate the medicinal materials. Traditionally, the authentication of Chinese herbs has relied upon morphological and histological inspection. For many biologic materials, this method is unreliable.

Eukaryotic genes for ribosomal RNA (rDNA) are normally clustered in an array of multiple tandemly repeated copies of the cistron of 18S-ITS1-5.8S-ITS2-28S (Hillis, and Dixon, 1991, The Quarterly Review of Biology, 66: 411-453). The sequence that separates the 18S and 5.8S rRNA genes is designated as ITS1 (Internal Transcribed Spacer 1) and the sequence between 5.8S and 28S is designated as ITS2. While the coding regions of the rDNA genes are highly similar, the sequence conservation within the ITS1 and ITS2 regions is much lower. Nevertheless, within a given individual organism or species, the sequences of rDNA ITS1 and ITS2 are usually similar as a result of gene conversion and crossing over. Methods have been developed based on the sequence polymorphism of rDNA ITS1 and ITS2 regions, such as the Polymerase Chain Reaction-Restriction Fragment Length Polymorphism (PCR-RFLP) technique. However, conventional methods of authenticating traditional Chinese medicinal materials are limited because they rely on the presence of suitable restriction enzyme cutting sites in the amplified DNA sequence. In the absence of an expected restriction enzyme cutting site, which may result from a sequence polymorphism, definitive authentication of a specimen is not possible. Another approach to determine a species origin for a biologic material has been the use of short specific probes for DNA hybridization assays. The success of this method is dependent on the identification of highly specific target sequences. When one highly specific target sequence cannot be identified, a combination of short hybridization probes can be used. However, this will increase the likelihood of obtaining false positive results. In addition, the low hybridization signals generated with hybridization assays often introduce another source of ambiguity in interpretation of the test result. Therefore, there is a need for a reliable method of authentication of biologic materials.

U.S. Pat. Nos. 5,876,977 and 6,309,840 disclose a PCR-RFLP based method for authenticating some species of plants used in Chinese medicinal materials based on differences in ribosomal RNA gene sequences.

SUMMARY OF THE INVENTION

The subject invention is directed to a method for authenticating biological samples using immobilized arrays of nucleic acids that include partial sequences of genes encoding ribosomal RNA (rDNA) and a kit for the authentication. Also included are methods of making arrays containing variable rDNA regions that are useful in authenticating biologic samples, such as traditional Chinese medicinal materials, and methods for amplifying rDNA from biologic samples of unknown origin, using primers that anneal to conserved ITS sequences. The amplified regions are used as probes in hybridization assays, the intensity of the hybridization signal increasing with fragment size. Probes amplified from authentic samples differ from other probes in the strength of the hybridization signal generated following hybridization with arrays of nucleic acid fragments of the respective authentic species or strain. The results obtained distinguish between minor sequence variations characteristic of intra-species or strain polymorphism and sequence divergences characteristic of different species, subspecies, or strains. The invention is useful to determine whether biological samples contain known species or strains, such as of traditional Chinese medicinal materials and to differentiate among related species or strains.

Accordingly, an object of the invention is to provide a method for preparing an array for authenticating whether a plant sample is originated from a known plant. The method comprises the steps of:

a) extracting DNAs from the known plant;

b) amplifying variable regions from the extracted DNAs to obtain nucleotide sequences of the variable regions;

c) designing specific primers according to the nucleotide sequences;

d) amplifying the variable regions by nested-PCR with the specific primers to obtain DNA fragments; and e) dotting the DNA fragments onto a solid support.

Another object of the present invention is to provide an array defined herein.

Still another object of the invention is to provide a An array for authenticating whether a plant sample is originated from a known plant, which is prepared by the steps of:

a) extracting DNAs from the known plant;

b) amplifying variable regions from the extracted DNAs to obtain nucleotide sequences of the variable regions;

c) designing specific primers according to the nucleotide sequences;

d) amplifying the variable regions by nested-PCR with the specific primers to obtain DNA fragments; and e) dotting the DNA fragments onto a solid support.

Yet another object of the invention is to provide A method for determining whether a plant sample is originated from a known plant, wherein the method comprises:

a) extracting first DNAs from the known plant;

b) amplifying variable regions from the extracted first DNAs to obtain nucleotide sequences of the variable regions;

c) designing specific primers according to the nucleotide sequences;

d) amplifying the variable regions by nested-PCR with the specific primers to obtain DNA fragments; and e) dotting the DNA fragments onto a solid support to obtain an array;

f) extracting second DNAs and third DNAs from the plant sample and the known plant, respectively;

g) respectively amplifying the variable regions from the extracted second and third DNAs to produce sample probes and control probes which are derived from the known plant;

h) hybridizing the sample and control probes with the array, respectively to obtain corresponding hybridization signals; and i) processing the hybridization signals to determine whether the plant sample is originated from the known plant.

In one preferred embodiment of the invention, the variable regions include ITSs, ETSs or IGRs, more preferably the variable regions are ITS 1 and ITS2.

The known plant used in the invention is preferably selected from *Ilex asprella, Ilex latifolia* or *Ilex rotunda*.

In one embodiment of the present invention, the specific primers comprise nucleotide sequences selected from the group consisting of: SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO:17, SEQ ID NO: 18, SEQ ID NO:19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO:45, SEQ ID NO: 46, SEQ ID NO: 47, SEQ ID NO: 48, SEQ ID NO: 49, SEQ ID NO: 50, SEQ ID NO: 51, SEQ ID NO:52, SEQ ID NO: 53, SEQ ID NO: 54, SEQ ID NO:55, and SEQ ID NO:56.

In another embodiment of the method for preparing an array of the present invention, the step b) may further comprises: amplifying the ITS1 region using primers IL-ITS1-143 (SEQ ID NO:7) and IL-ITS1-499R (SEQ ID NO:8) to reduce rRNA 18S and 5.8S regions flanking the ITS1 region of the nucleotide sequences.

In the invention, the ITS1 region preferably comprises a sequence selected from the group consisting of SEQ ID NO:1, SEQ ID NO:2 and SEQ ID NO:3, and the ITS2 region preferably comprises a sequence selected from the group consisting of: SEQ ID NO:4, SEQ ID NO:5 and SEQ ID NO:6.

In an embodiment of the method for authenticating plant samples, the processing comprises comparing the hybridization values of the sample probes to those of the control probes to see whether both of them are identical or plotting a graph of the length of the fragments versus corresponding values of the hybridization signals, and linearly regressing the graph or a combination thereof.

DETAILED DESCRIPTION OF SPECIFIC EMBODIMENTS

Figure 1:
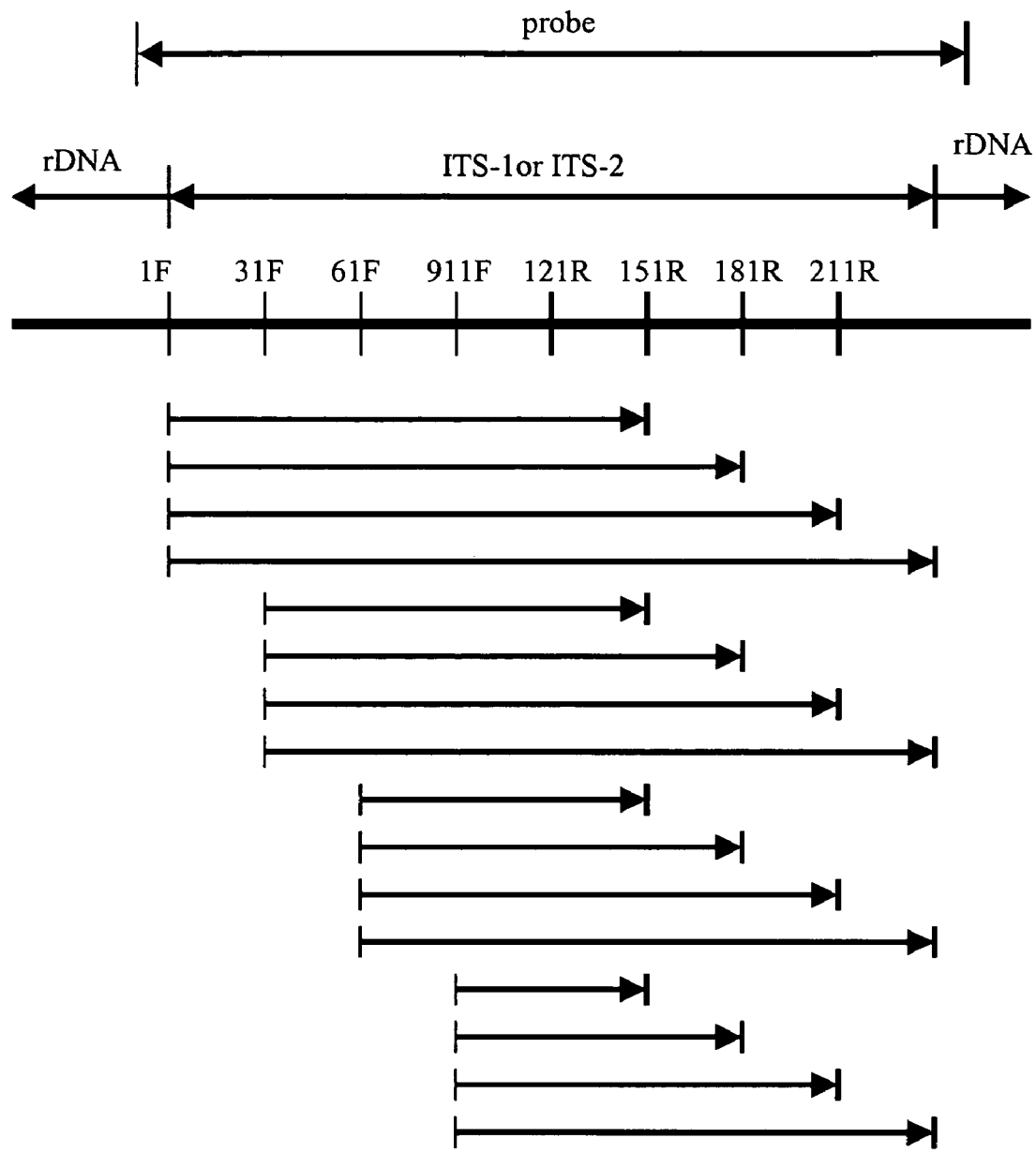
FIG. 1 is a diagram showing an amplification scheme for ITS1 and ITS2 fragments, in which the numbers indicate primers used and the arrows indicate the fragments' size (not to scale).

As described above, methods and kits useful for authentication of biological samples are provided. The method of making arrays for use in the authentication method includes the following steps. Variable rDNA regions of biologic samples, such as plants of the *Ilex* species, are isolated and an array of DNA fragments of various lengths and overlapping sequences corresponding to the variable rDNA regions isolated is generated. The sequences are then immobilized on a solid support, preferably as an addressable array. In the method for authenticating biologic samples, sample and control probes are contacted with the array and the intensity of the signal generated as compared to the control is used as an indication of the authenticity of the sample. The probes are obtained by amplification of ITS regions in a sample using a multiplicity of primers designed to anneal at highly conserved DNA sequences that flank variable rDNA regions.

The present invention utilizes variable regions of DNA sequences that are flanked by two highly conserved DNA regions. rDNA is suitable for use in the present invention because variable spacers separate conserved sequences encoding rRNA. Thus, primers that anneal to conserved sequences can be used for the amplification of sequences that may be unknown, or contain some differences from known spacer sequences.

In eukaryotic cells, the ribosomal RNA genes (rDNA) are organized somewhat differently than in prokaryotic (bacterial) cells. The prokaryotic rRNA gene cluster is composed of the 16S RNA gene followed by the 23S and 5S genes. Two IGRs (Inter-Genes Regions) are highly variable between the three structural genes. They are transcribed with the genes to give a precursor RNA of about 5200 nucleotides, but are removed by ribonuclease cutting of the total transcript. A promoter of transcription is located just before the 16S gene and a transcriptional terminator is located just beyond the 5S gene.

In eukaryotes a much larger initial transcript is made, typically about 13,000 nucleotides long. Before the 18S gene is ETS1, the first external transcribed spacer. A second external spacer is located just beyond the 28S gene. Two highly variable internal transcribed spacers, ITS1 and ITS2, are located between the 18S and 5.8S and between the 5.8S and 28S genes, respectively. There are approximately 2300 nucleotides in the 18S RNA, 160 nucleotides in the 5.8S RNA and some 4200 nucleotides in the 28S RNA. In all eukaryotes multiple copies of this rRNA gene cluster are found in the nucleolus, and there may be several nucleoli inside the nucleus of a single cell. In the nucleolus the rRNAs are transcribed, matured (cut) and assembled (along with the 5S RNA and 80 proteins) into ribosomes.

Embodiments of the invention can make use of any variable rDNA region, which may involve ITSs, ETSs, or IGRs, depending on the nature of the biological materials of interest. Variable rDNA regions from different eukaryotic species are typically characterized by significant sequence divergence, while corresponding regions of individuals of the same eukaryotic species contain less variation. In addition, prokaryotic strains or subspecies are often identifiable based on variations of sequences of rDNA regions (see for example U.S. Pat. No. 6,395,475). A preferred embodiment of the present invention uses ITS regions of eukaryotic traditional Chinese medicinal materials.

Variable rDNA regions of biological materials can be obtained by any methods known to the art. They can be conveniently isolated using Polymerase Chain Reaction (PCR) with primers that anneal at flanking conserved sequences. Such primers can be routinely designed based on known conserved rRNA sequences. Illustrative examples of suitable sequences for primers for amplifying variable rDNA regions can be found in Hillis, D. M and Dixon, M. T., 1991, The Quarterly Review of Biology, 66: 411-453, or White, T., et al., in PCR protocols: a guide to methods and applications, Innis, M., Gelfand, D., Sninsky, J., and White, T., eds., Academic Press, New York (1990) pp. 315-322, or U.S. Pat. No. 6,395,475. Isolation of ITS regions of traditional Chinese medicinal materials, such as SEQ ID NOs: 1-6, is exemplified below, and in U.S. Pat. No. 6,309,840.

According to the invention, a PCR primer (or, an oligonucleotide primer) is an oligonucleotide capable of specific hybridization under particular PCR conditions to a region of the template DNA, which has a sequence which is substantially complementary to the primer sequence, and is adapted to prime the extension of DNA during PCR. It will be realized that a complementary sequence is capable of forming Watson-Crick bonds with its complement, in which adenine pairs with thymine or guanine pairs with cytosine. Each primer is typically used as a member of a primer pair, including a 5' upstream primer that hybridizes with the 5' end of the template DNA to be amplified and a 3' downstream primer that hybridizes with the complement of the 3' end of the template DNA to be amplified. Those of ordinary skill in the art to which the invention relates will understand that the term "substantially complementary", as used herein, means that the primer may not have 100% complementarity to its target template sequence but is still capable of annealing thereto in a specific manner under appropriate PCR annealing conditions. Primers useful in connection with the present invention may be prepared by conventional DNA synthesis methods.

PCR is well known to skilled artisans in the fields of molecular biology and genetic engineering, and is described in general terms and with operational detail in, for example, "Current Protocols in Molecular Biology", Ausubel et al., John Wiley and Sons, New York 1987 (updated quarterly); "Molecular Cloning: A Laboratory Manual", 2nd Ed., Sambrook, Fritsch and Maniatis, Cold Spring Harbor Laboratory, Cold Spring Harbor, N.Y., 1989; "PCR Protocols: A Guide to Methods and Applications", Innis et al., Academic Press, NY 1990; and U.S. Pat. No. 4,965,188 issued on Oct. 23, 1990 to Mullis et al. As used herein, the term "PCR" relates to a procedure whereby a limited segment of a nucleic acid molecule, which frequently is a desired or targeted segment, is amplified repetitively to produce a large amount of DNA molecules which consist only of the segment. The procedure depends on repetition of a large number of replication cycles. In each cycle, two oligonucleotide primers bind to the segment, and define the limits of the segment. A primer-dependent DNA polymerase then transcribes, or replicates, the strands to which the primers have bound. Thus in each cycle, the number of DNA duplexes is doubled.

A typical template for isolation of variable rDNA regions in the present invention is genomic DNA. Isolation of suitable templates depends on biological materials of interest. For example, for prokaryotes it is often sufficient to suspend one or several colonies in 50 µl 10 mM EDTA in a microcentrifuge tube which is then put in boiling water for about five minutes, and the resulting lysate contains suitable DNA template. For eukaryotes, more sophisticated methods of extraction of genomic DNA known to the art may be applied if necessary.

In preferable embodiments of the invention, the obtained variable rDNA regions are sequenced. Sequencing can be accomplished by any nucleic acid sequencing procedures known to the art. When the variable rDNA regions are obtained by PCR amplification with primers based on adjacent conserved sequences, it is convenient to use the amplification primers for direct sequencing. Sequencing both strands of the amplification product is preferable to eliminate sequencing errors. While obtaining the full-length sequence of isolated rDNA regions is desirable, it is not absolutely necessary in many embodiments.

Arrays of nucleic acid fragments are produced based on the obtained variable rDNA regions in the invention. The nucleic acid fragments may be either single or double stranded, which are usually DNAs. To produce fragments consisting of partial sequences, a number of approaches may be employed. Among the options is digestion with restriction enzymes, limited exonuclease treatment, or in vitro synthesis. In a preferred embodiment, however, a nested PCR procedure is used. By "nested PCR" is meant a technique of producing DNA molecules of various lengths and overlapping sequences by amplification of distinct fragments using a combination of several forward and reverse primers that anneal at distinct sites on the variable rDNA region. For example, at least one forward primer is used in amplification reactions with two or more reverse primers, or vice versa. The length of DNA fragments obtained by the nested PCR is defined by the choice of primers. The length of any nucleic acid fragments can also be easily ascertained by methods known to the art, such as agarose gel electrophoresis. Thus, the nucleic acid fragments contain partial sequences of their variable rDNA region templates, although it is understood that such "fragments" may actually contain full-length sequences.

The primers for the nested PCR are designed based on the determined sequence of variable rDNA regions. Thus, a partial rather than full-length sequence of the variable rDNA regions obtained may be sufficient in some cases for effective primer design. In some embodiments, the arrays contain fragments of variable rDNA regions from several species or strains. In these cases, it is desirable to design the nested PCR primers to amplify relatively equivalent fragments of the various species of strains. Such a design facilitates comparison of hybridization signals from the same probe hybridized to equivalent fragments of different species or strains.

The hybridization potential of the nucleic acid fragments obtained to probes amplified from biological samples, such as putative Chinese medicinal materials, is measured. While in some cases hybridization of nucleic acids may be carried out and measured with molecules dissolved in a liquid phase, it is desirable to make an array of nucleic acid fragments by immobilization on a solid support. Binding of nucleic acids to membranes or beads is well known to the art. Double stranded nucleic acids are often denatured prior to immobilization to enhance their ability to hybridize to subsequently added probes. In some embodiments the array is a high-density polynucleotide array, sometimes called a DNA chip, as disclosed for example in U.S. Pat. Nos. 6,451,536, 6,410,229, and 6,329,140.

Nucleic acid probes from biological samples are amplified to assay their hybridization potential to the nucleic acid fragments in the array. Amplification typically by PCR as discussed above for the amplification of variable rDNA regions of authentic biological materials of interest. Primers that anneal to conserved sequences that flank variable rDNA regions are most helpful because they are useful in amplification of probes from a range of biological samples despite the their genetic variability. The same primers that were used in obtaining the variable rDNA region for making the array are often adequate for amplification of nucleic acid probes from samples. Alternatively, other primers may be designed based on sequences determined to be common to a subset of species, such as Chinese medicinal materials. Such alternative primer design can enhance the specificity of hybridization in some cases by eliminating conserved sequences from the amplified probes. Some embodiments employ both sample probes, amplified from tested biological samples, and control probes, amplified from authentic biological materials. In these embodiments it is preferable to amplify both the sample and the control probes with the same primers.

The amplified probe is typically labeled. Hybridization of unlabeled molecules may also be monitored, such as by changes in light or UV absorbance of a hybridization solution. It is preferable, however, to label the probe so as to be able to quantify the amount of probe hybridized to nucleic acid fragments in an array as proportional to the amount of label detectable. In those embodiments that employ both sample and control probes, it is desirable to label both probes with the same type of label and under similar conditions to facilitate the comparison of hybridization results, which are based on measurements of label bound to immobilized fragments.

Depending on the type of label chosen, in some embodiments of the invention probe amplification and labeling can be achieved in a single step. The label incorporated into the probe at one or more nucleotides may be, by way of non-limiting examples, radioactive, biotin, enzymes, digoxigenin, fluorescent probes, spectroscopic labels, chemiluminescent, bio-luminescent, and calorimetric labels. Radioactive labels include radioactive isotopes incorporated into the structure of the probe. Radioactive labels include, for example, $^{32}P$. This label can be detected by a phosphorimager. Detection, of course, depends on the resolution of the imager. Phosphorimagers are available having resolution of 50 microns. Accordingly, this label is useful with high-density arrays having features of at least that size. Biotin may be incorporated into the probe by use of biotinylated nucleotides. Biotin reacts specifically with streptavidin or avidin, which itself may be conjugated to an enzyme, the enzyme acting on a substrate to produce a detectable product. In one embodiment, biotinylated bases are incorporated into the target nucleic acid, and hybridization is detected by staining with streptavidin-phycoerythrin. Digoxigenin may be incorporated into the probe by use of digoxigenin-substituted nucleotides. Digoxigenin can be detected with a digoxigenin-specific antibody that likewise may be conjugated to an enzyme. Enzyme labels may also be conjugated directly to the probe. A common way of generating chemiluminescence is via an appropriate enzyme that acts on a substrate to produce light as one product of the reaction. Commercially available fluorescent labels include, inter alia, fluorescein phosphoramidites such as Fluoreprime (Pharmacia, Piscataway, N.J.), Fluoredite (Millipore, Bedford, Mass.) and FAM (ABI, Foster City, Calif.). Useful light scattering labels include large colloids, and especially the metal colloids such as those from gold, selenium, silver, tin, and titanium oxide.

Hybridization assays on substrate-bound polynucleotide arrays involve a hybridization step and a quantification step. In the hybridization step, a hybridization mixture containing the sample or control probe and, in some embodiments, a hybridization optimizing agent, such as an isostabilizing agent, denaturing agent or renaturation accelerant, is brought into contact with the fragments of the array and incubated at a temperature and for a time appropriate to allow hybridization between the nucleic acid fragments and any complementary probes. Usually, unbound probe molecules are then removed from the array by washing with a wash mixture that does not contain the probe, such as hybridization buffer. This leaves only bound probe molecules. In the quantification step, the hybridized probes are detected and measured. The measured hybridization values are typically expressed in relative units.

The hybridization mixture includes the probe and in some embodiments a hybridization-optimizing agent in an appropriate solution, i.e., a hybridization buffer. The probe is present in the mixture at a concentration typically between about 0.005 nM and about 50 nM, but often between about 0.5 nM and 5 nM. Betaines and lower tetraalkyl ammonium salts are examples of isostabilizing agents. Denaturing agents are compositions that lower the melting temperature of double stranded nucleic acid molecules by interfering with hydrogen bonding between bases in a double-stranded nucleic acid or the hydration of nucleic acid molecules. Denaturing agents include formamide, formaldehyde, DMSO (dimethylsulfoxide), tetraethyl acetate, urea, GuSCN, glycerol and chaotropic salts. Hybridization accelerants include heterogeneous nuclear ribonucleoprotein ("hnRP") A1 and cationic detergents such as, preferably, CTAB ("cetyltrimethylammonium bromide") and DTAB ("dodecyl trimethylammonium bromide"), and also, polylysine, spermine, spermidine, single stranded binding protein ("SSB"), phage T4 gene 32 protein and a mixture of ammonium acetate and ethanol.

The hybridization mixture is placed in contact with the array and incubated. Contact can take place in any suitable container, for example, a dish or a cell specially designed to hold the array and to allow introduction of the fluid into and removal of it from the cell so as to contact the array. Generally, incubation will be at temperatures normally used for hybridization of nucleic acids, for example, between about 20° C. and about 75° C., e.g., about 25° C., about 30° C., about 35° C., about 40° C., about 45° C., about 50° C., about 55° C., about 60° C., or about 70° C. For shorter probes or nucleic acid fragments, lower temperatures are preferred. The probe is incubated with the array for a time sufficient to allow the desired level of hybridization between the probe and any complementary nucleic acid fragments in the array.

After incubation with the hybridization mixture, the array usually is washed with the hybridization buffer, which also can include hybridization-optimizing agents. These agents can be included in the same range of amounts as for the hybridization step, or they can be eliminated altogether. Then the array can be examined to detect and quantify the probes hybridized to nucleic acid fragments.

Stringency conditions useful in the practice of the present invention are set forth, for example, in Sambrook et al., Molecular Cloning: A Laboratory Manual, 2d Ed. (1989). It is appreciated by those skilled in the art that non-specific hybridization decreases at high stringency. A high stringency with a condition of, for example, about 5×SSC and 68° C. is necessary in many embodiments. Acceptable stringency conditions may be pre-determined for species or strains of interest and the specific arrays. Thus, stringency conditions can be optimized by taking into account such factors as the length of the nucleic acid fragments in the array and probes, and any known degree of divergence of the variable rDNA regions or polymorphism of genetic material. If polymorphism exists that is known to affect hybridization under certain conditions, arrays can be optimized by including fragments that incorporate known polymorphism.

To practice the invention, it is often convenient to have useful reagents supplied as a kit. Thus, a kit might include an array and primers designed to function with biological samples, such as traditional Chinese medicinal materials, for which the array was designed. Optionally, kits may include authentic samples for use as controls. Such samples may be in unpurified form, to be processed in parallel to the samples tested, or may be purified nucleic acids. Kits might also include any useful components such as amplification and labeling reagents or optimum hybridization conditions information as well as a specification to indicate how to use the components in the kit.

The specific embodiment of the invention dictates the type of analysis of hybridization data necessary to authenticate biological samples. The hybridization of a probe to each nucleic acid fragment in an array is quantified. Thus, a set of hybridization values is obtained, with one value corresponding to each nucleic acid fragment in the array. One way to interpret the hybridization data is by comparison of a set of sample hybridization values to a set of control hybridization values. The sample hybridization values are obtained with a probe amplified from the biological sample tested. The control hybridization values are obtained with a probe amplified from an authentic species or strain from which the array was derived. Control values may be obtained from parallel hybridization to identical arrays, sequential hybridization to the same array, or may be predictable for defined hybridization conditions based on prior measurements. Thus, comparing each value in the sample hybridization set to the corresponding value of the control hybridization set provides an indication of whether the sample probe is derived from an authentic species or strain. When the sample tested is from an authentic species, the sample hybridization values are relatively equal to the control hybridization value. Because some level of error in the measurement of hybridization potential is expected, resemblance of sets of hybridization values may be appreciated in light of knowledge of hybridization values typical of "negative" control probes, i.e. probes amplified from samples known not to be authentic. Thus, when the sample tested is from an authentic material, not only are the sample values relatively equal to control values, but both sample and control values are also larger compared to corresponding negative control values. Alternatively, if the sample tested is not amplified from an authentic species or strain, the sample hybridization values are lower than the control hybridization values of the corresponding set, thus resembling results obtained with "negative" control probes. Use of a large number of nucleic fragments in the array that are derived from each variable rDNA region minimizes the possibility of obtaining inconclusive results.

To ensure accurate interpretation, additional analysis of the results may be performed. Thus, each nucleic acid fragment in the array has a known, defined length. Therefore, two numbers are associated to each nucleic acid fragment: one is the hybridization value and the other is the fragment's length. The hybridization value of control probes increases approximately linearly with the length of the corresponding nucleic acid fragment. An increase is often not seen with probes amplified from unrelated materials, i.e. only a background hybridization signal is measured regardless of the length of the nucleic acid fragment in the array. If some increase of sample hybridization value with fragment length is apparent, the increase is compared to the control linear increase. It may be convenient to plot a graph of the length of the fragments versus corresponding hybridization values, and the corresponding linear regressions, although the same type of analysis can be based on the numbers representing the calculated slopes of the linear regressions. Additional insights can come from comparison of subsets of hybridization values from sequence-related DNA fragments. For example, the linear relationship of probe hybridization value with fragment length may be better defined for fragments that share some sequence, such as those amplified with the same forward or reverse primer. Thus, definitive insights can be gained from comparison of subsets of sample hybridization values to corresponding subsets of control hybridization values. In sum, authenticity can be indicated by resemblance of sample and control hybridization values obtained from identical nucleic acid fragments, from linear regression slopes of hybridization values with fragment length calculated for all or a subset of related fragments in the array, or from a combination of these methods.

An alternative or additional approach to interpretation of results is based on arrays that contain nucleic acid fragments form a group of different species or strains. By a group it is meant at least two different species or strains. When arrays of homologous variable rDNA regions from different species or strains are used, authentication is possible based on markedly higher hybridization values of sample probes to fragments from only one species or strain. Sets of markedly larger hybridization values are characterized by significantly higher hybridization values to most DNA fragments of the set relatively to sets of different species or strains. It is preferable that fragments in the array from different species be designated as equivalent. For example, a fragment containing about 100 bp of the 5' ITS1 sequence of one species would be the equivalent of a fragment of about 100 bp of the 5' ITS1 sequence of other species. Comparison of hybridization values of sample probes to equivalent fragments can provide an additional indication of the identity of the sample. Comparison of the slopes of linear regressions of at least subsets of hybridization values with corresponding fragment lengths for each species is also informative in many cases. Finally, knowledge of results obtained with control probes from each species or strain under similar hybridization conditions can also be helpful in interpreting test data. This array design minimizes the possibility of obtaining inconclusive or incorrect test results.

The invention provides many advantages over the prior art. The analysis according to the present invention requires only minute samples. Unlike other techniques based on analysis of amplified ITS1 or ITS2 regions, sequence polymorphism that occurs within a species or strain does not affect the reliability of test results. Such sequence variations between authentic samples tested and standard specimens may comprise differences in the length of the amplified probes or insertion or deletion of specific restriction enzyme sites. Even in these cases, unlike prior techniques, the present invention enables an unambiguous determination of whether the tested sample comprises a known species, such as a traditional Chinese medicinal material. In addition, embodiments of the invention readily allow parallel comparison of an unknown sample to a large number of different known species or strains.

The following examples are offered by way of illustration and not by way of limitation.

EXAMPLES

Example 1

Extraction of Plant DNA

DNA was extracted from all the Chinese Medicinal Plants by FastDNA® Kit (BIO 101) and FP120 FastPrep™ Cell Disruptor (BIO 101), followed by treatment with RNase A and phenol/chloroform purification. First, about 150 mg of the sample was transferred into the Lysing Matrix tube, which contained a ¼" Sphere, Garnet, and ¼" Cylinder. Secondly, 800 µl Cell Lysis Solubilizing Solution (CLS-VF), 200 µl Protein Precipitation Solution (PPS), 1% polyvinylpyrolidone (PVP), 10 mM DTT, 10 mM sodium thiosulfate, and 2% beta-mercaptoethanaol were added to the tube. Thirdly, the tube was placed into the FastPrep™ Cell Disruptor and it was processed for 30 seconds at the speed setting of 5.0. Then, the sample was incubated at room temperature for 1 hour. After that, the tube was microcentrifuged at 14,000 rpm for 15 minutes to pellet protein and cell debris. About 600 µl of the supernatant was transferred to a new microcentrifuge tube and 5 µl of 10 mg/ml RNase A was added. After incubation for 1 hour at 37° C., 600 µl of Binding Matrix was added to the tube and mixed gently. After incubation for 5 minutes at room temperature, the tube was spun for 1 minute and the supernatant was discarded. The pellet was gently resuspended with 500 µl Salt-Ethanol Wash Solution (SEWS-M) and then it was spun for 1 minute and the supernatant was discarded. The liquid remaining was removed by suction. After that, DNA was eluted from the Binding Matrix by gently resuspending in 100 µl DNA Elution Solution (DES) followed by a 2-3 minutes period of incubation. The tube was spun for 1 minute at 14,000 rpm and the supernatant was transferred to a new tube. Then 400 µl water was added to increase the final volume. 1 volume of phenol chloroform: isoamyl alcohol (25:24:1) was added and the mixture was centrifuged at 14,000 rpm for 10 minutes. Then 1 volume of chloroform was added to the upper phase and was centrifuged at 14,000 rpm for 5 minutes. 0.1 volume of 3M sodium acetate (pH 5.2) and 2 volumes of absolute ethanol were added to the upper phase. After keeping the tube at −20° C. for 30 minutes, it was centrifuged at 14,000 rpm for 30 minutes at 4° C. The supernatant was removed and the DNA pellet was dried in a SpeedVac (Savant). Finally, the pellet was dissolved in 100 ultra pure water and it was stored at −20° C. The concentration and purity of the DNA preparations were assayed by spectrophotometric measurements ($OD_{260}$ and $OD_{280}$), (Milton Roy Spectronic 3000, GeneQuant RNA/DNA Calculator). The quality of DNA was also examined afterwards by 1.0% agarose gel electrophoresis in 1×TBE buffer (prepared from 10×TBE stock solution which contains 0.9M Tris base, 0.9M boric acid and 0.002M EDTA).

Example 2

Amplification of the rRNA Gene Entire ITS1 and ITS2 Regions

The rRNA gene ITS1 and ITS2 regions were specifically amplified using primers 18B and 5.8C, and 5.8D and 28CC respectively (Hillis, D. M and Dixon, M. T., 1991, The Quarterly Review of Biology, 66: 411-453):

```
18B  (SEQ ID NO:57):  5' AGGAATGCCTAGTAAGCGCGAGTCAT
                        CAGCT 3'

5.8C (SEQ ID NO:58):  5' TTGCGTTCAAAGACTCGATGGTTCA
                        3'

5.8D (SEQ ID NO:59):  5' TGAACCATCGAGTCTTTGAACGCAA
                        3'

28CC (SEQ ID NO:60):  5' ACTCGCCGTTACTAGGGGAATCCTCG
                        TAAG 3'
```

The reaction was performed in a 100 µl mixture containing 10 ng DNA template, 0.2 mM dNTPs, 2.5 mM $MgCl_2$, 1× thermophilic DNA polymerase buffer, Promega (10 mM Tris-HCl, pH9.0, 50 mM KCl and 0.1% Triton®-100), 0.2 µM each specific primer), and 4U of Taq polymerase (Promega). Water was added to make up the final volume to 100 µl. The DNA template was denatured at 94° C. for 2 minutes, and then 40 cycles of 94° C. for 1 minute, 55° C. for 1 minute, 72° C. for 2 minutes were carried out. The final extension was carried out at 72° C. for 10 minutes. The amplification products were electrophoresed on a 1% agarose gel, stained with ethidium bromide, and observed under UV illumination.

Example 3

Sequencing of ITS1 and ITS2

The ITS1 and ITS2 regions of rRNA genes were sequenced in both strands after amplified. The ABI PRISM™ dRhodamine Terminator Cycle Sequencing ready Reaction Kit with AmpliTaq® DNA Polymerase, FS (Perkin-Elmer) was used to direct-sequence the PCR-amplified ITS regions. The cycle sequencing reaction was done according to the manufacturer's instruction. The cycle sequencing reaction products were resolved by capillary electrophoresis in 1× Genetic Analysis Buffer (Perkin Elmer) with the ABI PRISM™ 310 Genetic Analyzer.

Example 4

Primers Design

A pair of primers, IL-ITS1-143F and IL-ITS1-499R, was designed based on the sequence of the ITS1 region of the species *Ilex latifolia* with the PrimerExpress 1.0 software. Amplification of the entire ITS1 region using primers IL-ITS1-143F and IL-ITS1-499R instead of primers 18B and 5.8C reduced the portion of both of the flanking rRNA 18S and the 5.8S regions in the amplification products.

```
IL-ITS1-143F:
5' GAACCTGCGGAAGGATCATT 3'     (SEQ ID NO:7)

IL-ITS1-499R:
5' CGAGAGCCGAGATATCCGTT 3'     (SEQ ID NO:8)
```

Sets of primers were designed for the amplification of ITS1 and ITS2 fragments of three *Ilex* species: *Ilex asprella*, *Ilex latifolia* and *Ilex rotunda*. These primers, were designed based on the obtained sequences of the ITS regions. The primers are listed in tables 1 and 2.

TABLE 1

Nucleotide Sequences of Three Sets of 30mers Primers for the Amplification of the ITS1 Fragments for All 3 Ilex Species.

| Primers | Sequences |
|---|---|
| IA-ITS1-1F   | 5' CGATGCCTGCAAAGTAGACCCGGCGAACCT 3' (SEQ ID NO:9) |
| IA-ITS1-31F  | 5' GTTAAAATATGCCTGGGGGTTTGAGAAGGG 3' (SEQ ID NO:10) |
| IA-ITS1-61F  | 5' GTGCGCGAGCCCCCCGACACACTCCCCTAC 3' (SEQ ID NO:11) |
| IA-ITS1-91F  | 5' CTCGGGATTTGGCTTGCGTTCCCCCAGCGG 3' (SEQ ID NO:12) |
| IA-ITS1-121R | 5' GGGTTCGTTGTCGGGAGCTTGGCCGAGTCC 3' (SEQ ID NO:13) |
| IA-ITS1-151R | 5' GGTTAAGGTTCCTTGGCGCAGACAGCGCCG 3' (SEQ ID NO:14) |
| IA-ITS1-181R | 5' GCGAACGGGACATCGGGGGGCCAGCTCTTC 3' (SEQ ID NO:15) |
| IA-ITS1-211R | 5' AAAAGACGCGTATGCTTCCCGTTGCACACC 3' (SEQ ID NO:16) |
| IL-ITS1-1F   | 5' CGATGCCTGCAAAGTAGACCCGGCGAACTT 3' (SEQ ID NO:17) |
| IL-ITS1-31F  | 5' GTTAAAATATGCCTGGGGGTTTGAGAAGGG 3' (SEQ ID NO:18) |
| IL-ITS1-61F  | 5' GTGCGCGAGCCCCCCGACACACTCCCCCAG 3' (SEQ ID NO:19) |
| IL-ITS1-91F  | 5' CCCCCTCGGGATTTGGCTTGCGTTCCCCTA 3' (SEQ ID NO:20) |
| IL-ITS1-121R | 5' TCGTTGTCGGGAGCTTGACCGAGTCCCCGC 3' (SEQ ID NO:21) |
| IL-ITS1-151R | 5' ATGGTTCCTTGGCGCAGATAGCGCCGGGGT 3' (SEQ ID NO:22) |
| IL-ITS1-181R | 5' ACGGGACATCGGGAGGCCAGCCCTTCAGTT 3' (SEQ ID NO:23) |
| IL-ITS1-211R | 5' GATGCAGATGCCTCCCGTTGCACGCCGCGA 3' (SEQ ID NO:24) |
| IR-ITS1-1F   | 5' CGATGCCTGCAAAGTAGACCCGGCGAACTC 3' (SEQ ID NO:25) |
| IR-ITS1-31F  | 5' GTTAAAATATGCGTGGGGGTTTGAGAAGGG 3' (SEQ ID NO:26) |
| IR-ITS1-61F  | 5' GCGCGCGAGCCCCCCTCGACACACTCCCCC 3' (SEQ ID NO:27) |
| IR-ITS1-91F  | 5' ACCCCCCGGGACTTGGCGCGGGTTCCCCTT 3' (SEQ ID NO:28) |
| IR-ITS1-121R | 5' CGTTGTCGGGAGCCTTGGCCGAGTCCCCGC 3' (SEQ ID NO:29) |
| IR-ITS1-151R | 5' GGGTTCCTTGGCGCAGACAGCGCCGGGGTT 3' (SEQ ID NO:30) |
| IR-ITS1-181R | 5' GGGACACCGGGGGGCCAGCTCTTCGGTTAA 3' (SEQ ID NO:31) |
| IR-ITS1-211R | 5' ATGCGTACGCCTCCCGTGCACACCGCGAAC 3' (SEQ ID NO:32) |

TABLE 2

Nucleotide Sequences of Three Sets of 30mers Primers for the Amplification of the ITS2 Fragments for all 3 Ilex Species.

| Primers | Sequences |
|---|---|
| IA-ITS2-1F   | 5' CATCCCGTCGCCCCCCAACCCCAATGCCTA 3' (SEQ ID NO:33) |
| IA-ITS2-31F  | 5' GCTAGCTGGATATTGCGGGAGTTGGGGGCG 3' (SEQ ID NO:34) |
| IA-ITS2-61F  | 5' GAAATTGGCCTCCCGTCCACGACCGTGCGC 3' (SEQ ID NO:35) |
| IA-ITS2-91F  | 5' GGTTGGCCCAAAAAAGAAGAGCTCCTGACG 3' (SEQ ID NO:36) |
| IA-ITS2-121R | 5' CTTTCAACCACCACTTGTCGTGACGTCCGT 3' (SEQ ID NO:37) |
| IA-ITS2-151R | 5' CTCGGTGCCTCACGACATGATGCAAGAGGT 3' (SEQ ID NO:38) |
| IA-ITS2-181R | 5' CGCAGGGTCACGATCGGAGCTCGCCGGAGA 3' (SEQ ID NO:39) |
| IA-ITS2-211R | 5' GCGGTCGGAGCACCGTCCCGGGAGGAGGTG 3' (SEQ ID NO:40) |

TABLE 2-continued

Nucleotide Sequences of Three Sets of 30mers Primers for the Amplification of the ITS2 Fragments for all 3 Ilex Species.

| Primers | Sequences |
|---|---|
| IL-ITS2-1F | 5' CATCACGTCGCCACCAACCCCGATGCCCAG 3' (SEQ ID NO:41) |
| IL-ITS2-31F | 5' CTGGATATTAGCGGGAGTTGGGGGCGGAAA 3' (SEQ ID NO:42) |
| IL-ITS2-61F | 5' TTGGCCTCCCGTCCACGAACGTGCGCGGTT 3' (SEQ ID NO:43) |
| IL-ITS2-91F | 5' GGCCCAAAAAATGAGTTCTTGACGATGGAC 3' (SEQ ID NO:44) |
| IL-ITS2-121R | 5' AGAGGTCTTTCAACCACCACTTGCCGTGAC 3' (SEQ ID NO:45) |
| IL-ITS2-151R | 5' TACAGACTTGGTGCCTCACGACATGACGCA 3' (SEQ ID NO:46) |
| IL-ITS2-181R | 5' AGGGTGCACAGGGTCGCGGTCAGAGCTCGC 3' (SEQ ID NO:47) |
| IL-ITS2-211R | 5' GGTCGCGGTCGGAGCACCATCCGTGAAGGA 3' (SEQ ID NO:48) |
| IR-ITS2-1F | 5' CATCACGTCGCCCCCAACCCCGACAATGCC 3' (SEQ ID NO:49) |
| IR-ITS2-31F | 5' CGGCTGGCAGCCGGATATTGCGGGAGTTGC 3' (SEQ ID NO:50) |
| IR-ITS2-61F | 5' GGGCGGAGATTGGCCTCCCGTCCACGACCG 3' (SEQ ID NO:51) |
| IR-ITS2-91F | 5' TGCGCGGTTGGCCCAAAAAGCGAGTTCTTG 3' (SEQ ID NO:52) |
| IR-ITS2-121R | 5' CCAACCACCACTCGTCGTGACGTCCGTCGT 3' (SEQ ID NO:53) |
| IR-ITS2-151R | 5' GGTGCCTCACGACTCGACGCAAGAGGTCTT 3' (SEQ ID NO:54) |
| IR-ITS2-181R | 5' GGGTCGCGGTCAGAGCTCGTTACAGACTCG 3' (SEQ ID NO:55) |
| IR-ITS2-211R | 5' CGGAGCGCCGCCCCCTAAGGAAGGGGCACA 3' (SEQ ID NO:56) |

Example 5

Amplification of ITS1 and ITS2 Fragments

ITS fragments of both ITS1 and ITS2 were amplified with various primer combinations (Table 3a and 3b) following the PCR protocol described in "Amplification of the rRNA gene entire ITS1 and ITS2 regions" section. The temperature profile was: 94° C. for 2 minutes and then 40 cycles of 94° C. for 45 seconds, 55° C. for 30 seconds, 72° C. for 1.5 minutes, followed by 72° C. for 10 minutes as the final extension step. The amplification products were visualized on a 1% agarose gel stained with ethidium bromide under UV illumination.

TABLE 3

Primer Combinations Used for the Amplification of (a) ITS1 and (b) ITS2 Regions

| Forward Primers | Reverse Primers |
|---|---|
| (a) Primer Combinations | |
| IA161F* | IA281R |
|  | IA311R |
|  | IA341R |
|  | IA371R |
| IA191F | IA281R |
|  | IA311R |
|  | IA341R |
|  | IA371R |
|  | IA281R |
| IA221F | IA311R |
|  | IA341R |
|  | IA371R |
|  | IA281R |
| IA251F | IA311R |
|  | IA341R |
|  | IA371R |
| (b) Primer Combinations | |
| IA-ITS2-1F | IA-ITS2-121R |
|  | IA-ITS2-151R |
|  | IA-ITS2-181R |
|  | IA-ITS2-211R |
| IA-ITS2-31F | IA-ITS2-121R |
|  | IA-ITS2-151R |
|  | IA-ITS2-181R |
|  | IA-ITS2-211R |
| IA-ITS2-61F | IA-ITS2-121R |
|  | IA-ITS2-151R |
|  | IA-ITS2-181R |
|  | IA-ITS2-211R |
| IA-ITS2-91F | IA-ITS2-121R |
|  | IA-ITS2-151R |
|  | IA-ITS2-181R |
|  | IA-ITS2-211R |

*Primers containing "IA", "IL", and "IR" as part of their names amplify sequences of *Ilex asprella*, *Ilex latifolia* and *Ilex rotunda*, respectively.

Example 6

Preparation of Membranes

A dot-blot apparatus (Bio-Rad) was cleaned with double distilled water and ethanol to remove any oil present. Then, a positively charged nylon membrane (Hybond N+, Amersham) was fixed onto the dot-blot apparatus. The membrane was pre-wetted by dotting 400 µl ultra pure water. Denaturing solution was prepared by adding 20 µl of 2M NaOH and 165 µl of pure water into PCR tubes. Next, similar concentrations of the PCR products were added to denaturing solution and were incubated at room temperature for at least 15 minutes. After denaturation, all solution was dotted onto the membrane followed by addition of 400 µl 20×SSC (3M NaCl, 0.3M sodium citrate) to neutralize the NaOH. Finally the membrane was air-dried and baked at 80° C. for one hour to immobilize single-stranded DNA fragments on the membrane.

Example 7

Preparation of Probes

The entire ITS1 and ITS2 regions were amplified and served as the probes for dot-blot hybridization. DIG-High Prime (Boehringer Mannheim) was used to label the probes. 16 µl of purified template DNA was added to PCR tubes and the DNA was denatured by heating at 96° C. for 10 minutes, and then chilled on ice immediately after heating. 4 µl of DIG-High Prime [5× conc.: 1U/µl Klenow enzyme, 1 mM dATP, 1 mM dCTP, 1 mM dGTP, 0.65 mM dTTP, 0.35 mM alkali-labile DIG-11-dUTP, 5× stabilized reaction buffer in glycerol 50% (v/v)] was added to the tube. After brief mixing and centrifuging, the mixture was incubated at 37° C. for 20 hours (overnight). Finally, the reaction was stopped by heating the mixture at 65° C. for 10 minutes.

Example 8

Hybridization

The DIG Nucleic Acid Detection Kit (Boehringer Mannheim) was used in the hybridization and immunological detection steps. The hybridization buffer was prepared to a final concentration of 5×SSC (0.75M NaCl, 0.075M sodium citrate), 1% of Blocking reagent [Block Reagent in Buffer 1 (0.1M maleic acid, 0.15M NaCl, adjusted to pH7.5 with sodium hydroxide pellet)], 0.1% of N-lauroylsarcosine, 0.02% of SDS. The membrane was placed into a hybridization bottle and pre-soaked with hybridization buffer (20 ml for 100 cm²) at 68° C. for at least one hour. After that, the probe was denatured at 100° C. for 5 minutes. The solution in the hybridization bottle was then replaced by 2.5 ml per 100 cm² fresh hybridization buffer, which containing 12.5 µl of synthesized probe. Then the bottle was incubated at 68° C. for 20 hours.

After hybridization, the membrane was washed twice with about 100 ml 2×SSC+0.1% SDS solution at room temperature for 5 minutes. Then the membrane was further washed twice with about 100 ml 0.1×SSC+0.1% SDS solution at 68° C. for 15 minutes.

Example 9

Immunological Detection and Quantification

The following steps were performed at room temperature unless specified othewise. The membrane was washed briefly with Washing Buffer [1L Buffer 1, 0.3% (w/v) Tween-20®]. Then the membrane was incubated in about 100 ml Buffer 2 (1% Blocking Reagent in Buffer 1) for 30 minutes. The antibody, Anti-Digoxigenin-AP Conjugate, was centrifuged at 10,000 rpm for 5 minutes before dilution (150 mU/ml) in Buffer 2. Then the membrane was incubated in 20 ml diluted Anti-Digoxigenin-AP Conjugate solution for 30 minutes. After that, the membrane was washed twice with 100 ml Buffer 1 for 15 minutes. Finally the membrane was equilibrated with 20 ml of Detection Buffer (100 mM Tris-HCl, 100 mM NaCl, pH 9.5) for 2-5 minutes.

The CSPD® Working Solution (Roche Molecular Biochemicals) was prepared with the concentration of 10 µl in 1 ml of Detection Buffer. The membrane was placed with the DNA side facing up on a hybridization bag. Then, 1 ml of the CSPD® Working Solution was added onto the membrane. The membrane was then immediately covered with the second sheet of the bag to spread the substrate evenly and without air bubbles over the membrane. Next, the bag was sealed and incubated at room temperature for 5 minutes. The luminescent reaction was enhanced by incubating the bag at 37° C. for 10 minutes. Finally the membrane was exposed to the Lumi-Imager™ for 1-15 minutes (depending on the signal strength) at room temperate and the density of each dot was measured using the Lumi-Analyst software.

Example 10

Calculating Linear Regression

The density measured for hybridization of probes to each fragment was plotted against the corresponding fragment size shown in Table 4a and 4b.

TABLE 4

Relationship between the Product Size and the Primer Combinations of (a) ITS1 and (b) ITS2 Regions (a) Primer Combinations

| Combination No. | Forward Primers | Reverse Primers | Product Size (bp) |
|---|---|---|---|
| IA-a | IA-ITS1-1F | IA-ITS1-121R | 150 |
| IA-b | IA-ITS1-1F | IA-ITS1-151R | 180 |
| IA-c | IA-ITS1-1F | IA-ITS1-181R | 210 |
| IA-d | IA-ITS1-1F | IA-ITS1-211R | 240 |
| IA-e | IA-ITS1-31F | IA-ITS1-121R | 120 |
| IA-f | IA-ITS1-31F | IA-ITS1-151R | 150 |
| IA-g | IA-ITS1-31F | IA-ITS1-181R | 180 |
| IA-h | IA-ITS1-31F | IA-ITS1-211R | 210 |
| IA-I | IA-ITS1-61F | IA-ITS1-121R | 90 |
| IA-j | IA-ITS1-61F | IA-ITS1-151R | 120 |
| IA-k | IA-ITS1-61F | IA-ITS1-181R | 150 |
| IA-l | IA-ITS1-61F | IA-ITS1-211R | 180 |
| IA-m | IA-ITS1-91F | IA-ITS1-121R | 60 |
| IA-n | IA-ITS1-91F | IA-ITS1-151R | 90 |
| IA-o | IA-ITS1-91F | IA-ITS1-181R | 120 |
| IA-p | IA-ITS1-91F | IA-ITS1-211R | 150 |

(b) Primer Combinations

| Combination No. | Forward Primers | Reverse Primers | Product Size (bp) |
|---|---|---|---|
| IA-A | IA-ITS2-1F | IA-ITS2-121R | 150 |
| IA-B | IA-ITS2-1F | IA-ITS2-151R | 180 |
| IA-C | IA-ITS2-1F | IA-ITS2-181R | 210 |
| IA-D | IA-ITS2-1F | IA-ITS2-211R | 240 |
| IA-E | IA-ITS2-31F | IA-ITS2-121R | 120 |

TABLE 4-continued

Relationship between the Product Size and the Primer Combinations of (a) ITS1 and (b) ITS2 Regions

| | | | |
|---|---|---|---|
| IA-F | IA-ITS2-31F | IA-ITS2-151R | 150 |
| IA-G | IA-ITS2-31F | IA-ITS2-181R | 180 |
| IA-H | IA-ITS2-31F | IA-ITS2-211R | 210 |
| IA-I | IA-ITS2-61F | IA-ITS2-121R | 90 |
| IA-J | IA-ITS2-61F | IA-ITS2-151R | 120 |
| IA-K | IA-ITS2-61F | IA-ITS2-181R | 150 |
| IA-L | IA-ITS2-61F | IA-ITS2-211R | 180 |
| IA-M | IA-ITS2-91F | IA-ITS2-121R | 60 |
| IA-N | IA-ITS2-91F | IA-ITS2-151R | 90 |
| IA-O | IA-ITS2-91F | IA-ITS2-181R | 120 |
| IA-P | IA-ITS2-91F | IA-ITS2-211R | 150 |

Example 11

Results

Three species of the Chinese medicinal plants *Ilex asprella*, *Ilex latifolia* and *Ilex rotunda* were used to illustrate this invention. ITS1 region of rRNA gene was amplified using primers 18B and 5.8C, and ITS2 regions of rRNA gene was amplified with primers 5.8D and 28CC (Hillis, D. M and Dixon, M. T., 1991, The Quarterly Review of Biology, 66: 411-453). The sequences of these regions, shown in Tables 5 and 6, were obtained after direct sequencing of both strands of the PCR products.

TABLE 5

Nucleotide Sequences of rRNA Gene ITS1 Regions

| | | |
|---|---|---|
| *Ilex asprella* | 1 CGATGCCTGC AAAGTAGACC CGGCGAACCT GTTAAAATAT GCT-TGGGGGT<br>51 CTGAGAAGGG GTGCGCGAGC CCCCCGACAC ACTCCCCTAC CTCGG-GATTT<br>101 GGCTTGCGTT CCCCCAGCGG GGACTCGGCC AAGCTCCCGA CAAC-GAACCC<br>151 CGGCGCTGTC TGCGCCAAGG AACCTTAACC GAAGAGCTGG CCCCCCGATG<br>201 TCCCGTTCGC GGTGTGCACG GGAAGCATAC GCGTCTTTTG AAT | (SEQ ID NO:1) |
| *Ilex latifolia* | 1 CGATGCCTGC AAAGTAGACC CGGCGAACTT GTTAAAATAT GCCTGGGGGT<br>51 TTGAGAAGGG GTGCGCGAGC CCCCCGACAC ACTCCCCCAG CCCCCTCGGG<br>101 ATTTGGCTTG CGTTCCCCTA GCGGGACTC GGTCAAGCTC CCGA-CAACGA<br>151 ACCCCGGCGC TATCTGCGCC AAGGAACCAT AACTGAAGGG CTGGC-CTCCC<br>201 GATGTCCCGT TCGCGGCGTG CAACGGGAGG CATCTGCATC TTTTGAAT | (SEQ ID NO:2) |
| *Ilex rotunda* | 1 CGATGCCTGC AAAGTAGACC CGGCGAACTC GTTAAAATAT GCGTGGGGGT<br>51 TTGAGAAGGG GCGCGCGAGC CCCCCTCGAC ACAATTCCCC CAC-CCCCCGG<br>101 GACTTGGCCC GGGTTCCCCT TGCGGGGACT CGGCCAAGGC TCCCGA-CAAC<br>151 GAACCCCGGC GCTGTCTGCG CCAAGGAACC CTTAACCGAA GAGCTG-GCCC<br>201 CCCGGTGTCC CGTTCGCGGT GTGCACGGGG GGCGTACGCA TCTTTC-GAAT | (SEQ ID NO:3) |

TABLE 6

Nucleotide Sequences of rRNA Gene ITS2 Regions

| | | |
|---|---|---|
| *Ilex asprella* | 1 CATCCCGTCG CCCCCCAACC CCAATGCCTA GCTAGCTGGA TAT-TGCGGGA<br>51 GTTGGGGGCG GAAATTGGCC TCCCGTCCAC GACCGTGCGC GGTTG-GCCCA<br>101 AAAAAGAAGA GCTCCTGACG ACGGACGTCA CGACAAGTGG TGGT-TGAAAG<br>151 ACCTCTTGCA TCATGTCGTG AGGCACCGAG TCTCCGGCGA GCTC-CGATCG<br>201 TGACCCTGCG CACCTCCTCC CGGGACGGTG CTCCGACC | (SEQ ID NO:4) |
| *Ilex latifolia* | 1 CATCACGTCG CCACCAACCC CGATGCCCAG CTGGATATTA GCGG-GAGTTG<br>51 GGGGCGGAAA TTGGCCTCCC GTCCACGAAC GTGCGCGGTT GGC-CCAAAAA<br>101 ATGAGTTCTT GACGATGGAC GTCACGGCAA GTGGTGGTTG AAAGAC-CTCT<br>151 TGCGTCATGT CGTGAGGCAC CAAGTCTGTA GCGAGCTCTG ACCGC-GACCC<br>201 TGTGCACCCT TCCTTCACGG ATGGTGCTCC GACC | (SEQ ID NO:5) |

TABLE 6-continued

Nucleotide Sequences of rRNA Gene ITS2 Regions

```
Ilex rotunda    1 CATCACGTCG CCCCCAACCC CGACAATGCC CGGCTGGCAG CCG-    (SEQ ID NO:6)
                  GATATTG
               51 CGGGAGTTGC GGGCGGAGAT TGGCCTCCCG TCCACGACCG TGCGCG-
                  GTTG
              101 GCCCAAAAAG CGAGTTCTTG ACGACGGACG TCACGACGAG TGGTG-
                  GTTGG
              151 AAGACCTCTT GCGTCGAGTC GTGAGGCACC CGAGTCTGTA
                  ACGAGCTCTG
              201 ACCGCGACCC TGTGCGCCTT CCTTAGGGGG CGGCGCTCCG AC
```

For each ITS region, i.e. ITS1 and ITS2, sets of primers were synthesized based on the ITS sequences of the three *Ilex* species. Each *Ilex* species had its own set of primers, each set consisting of 8 primers having the length of 30 nucleotides. Moreover, primers IL-ITS1-143F (SEQ ID NO:7) and IL-ITS1-499R (SEQ ID NO:8) were constructed to replace primers 18B and 5.8C for the amplification of entire ITS1 region for all 3 *Ilex* species. These two primers were constructed in such a way that they flanked the ITS1 region so as to reduce the portion of both the rDNA 18S and the 5.8S regions in the amplification products. The primers used in generating the arrays of DNA fragments were shown in Tables 7 and 8.

TABLE 7

Nucleotide Sequences of Three Sets of 30mer Primers for the Amplification of the ITS1 Fragments of Three Ilex Species

| PRIMERS | SEQUENCES | SEQ ID NO: |
|---|---|---|
| IA-ITS1-1F:   | 5' CGATGCCTGCAAAGTAGACCCGGCGAACCT 3' | (SEQ ID NO:9) |
| IA-ITS1-31F:  | 5' GTTAAAATATGCCTGGGGGTTTGAGAAGGG 3' | (SEQ ID NO:10) |
| IA-ITS1-61F:  | 5' GTGCGCGAGCCCCCCGACACACTCCCCTAC 3' | (SEQ ID NO:11) |
| IA-ITS1-91F:  | 5' CTCGGGATTTGGCTTGCGTTCCCCCAGCGG 3' | (SEQ ID NO:12) |
| IA-ITS1-121R: | 5' GGGTTCGTTGTCGGGAGCTTGGCCGAGTCC 3' | (SEQ ID NO:13) |
| IA-ITS1-151R: | 5' GGTTAAGGTTCCTTGGCGCAGACAGCGCCG 3' | (SEQ ID NO:14) |
| IA-ITS1-181R: | 5' GCGAACGGGACATCGGGGGCCAGCTCTTC 3' | (SEQ ID NO:15) |
| IA-ITS1-211R: | 5' AAAAGACGCGTATGCTTCCCGTTGCACACC 3' | (SEQ ID NO:16) |
| IL-ITS1-1F:   | 5' CGATGCCTGCAAAGTAGACCCGGCGAACTT 3' | (SEQ ID NO:17) |
| IL-ITS1-31F:  | 5' GTTAAAATATGCCTGGGGGTTTGAGAAGGG 3' | (SEQ ID NO:18) |
| IL-ITS1-61F:  | 5' GTGCGCGAGCCCCCCGACACACTCCCCCAG 3' | (SEQ ID NO:19) |
| IL-ITS1-91F:  | 5' CCCCCTCGGGATTTGGCTTGCGTTCCCCTA 3' | (SEQ ID NO:20) |
| IL-ITS1-121R: | 5' TCGTTGTCGGGAGCTTGACCGAGTCCCCGC 3' | (SEQ ID NO:21) |
| IL-ITS1-151R: | 5' ATGGTTCCTTGGCGCAGATAGCGCCGGGGT 3' | (SEQ ID NO:22) |
| IL-ITS1-181R: | 5' ACGGGACATCGGGAGGCCAGCCCTTCAGTT 3' | (SEQ ID NO:23) |
| IL-ITS1-211R: | 5' GATGCAGATGCCTCCCGTTGCACGCCGCGA 3' | (SEQ ID NO:24) |
| IR-ITS1-1F:   | 5' CGATGCCTGCAAAGTAGACCCGGCGAACTC 3' | (SEQ ID NO:25) |
| IR-ITS1-31F:  | 5' GTTAAAATATGCGTGGGGGTTTGAGAAGGG 3' | (SEQ ID NO:26) |
| IR-ITS1-61F:  | 5' GCGCGCGAGCCCCCCTCGACACACTCCCCC 3' | (SEQ ID NO:27) |
| IR-ITS1-91F:  | 5' ACCCCCCGGGACTTGGCCCGGGTTCCCCTT 3' | (SEQ ID NO:28) |
| IR-ITS1-121R: | 5' CGTTGTCGGGAGCCTTGGCCGAGTCCCCGC 3' | (SEQ ID NO:29) |
| IR-ITS1-151R: | 5' GGGTTCCTTGGCGCAGACAGCGCCGGGGTT 3' | (SEQ ID NO:30) |
| IR-ITS1-181R: | 5' GGGACACCGGGGGGCCAGCTCTTCGGTTAA 3' | (SEQ ID NO:31) |

TABLE 7-continued

Nucleotide Sequences of Three Sets of 30mer Primers for the Amplification of the ITS1 Fragments of Three Ilex Species

| PRIMERS | SEQUENCES | SEQ ID NO: |
|---|---|---|
| IR-ITS1-211R: | 5' ATGCGTACGCCTCCCGTGCACACCGCGAAC 3' | (SEQ ID NO:32) |
| IL-ITS1-143F: | 5' GAACCTGCGGAAGGATCATT 3' | (SEQ ID NO:7) |
| IL-ITS1-499R: | 5' CGAGAGCCGAGATATCCGTT 3' | (SEQ ID NO:8) |

TABLE 8

Nucleotide Sequences of Three Sets of 30mer Primers for the Amplification of the ITS2 Fragments of Three Ilex Species

| PRIMERS | SEQUENCES | SEQ ID NO: |
|---|---|---|
| IA-ITS2-1F: | 5' CATCCCGTCGCCCCCAACCCCAATGCCTA 3' | (SEQ ID NO:33) |
| IA-ITS2-31F: | 5' GCTAGCTGGATATTGCGGGAGTTGGGGCG 3' | (SEQ ID NO:34) |
| IA-ITS2-61F: | 5' GAAATTGGCCTCCCGTCCACGACCGTGCGC 3' | (SEQ ID NO:35) |
| IA-ITS2-91F: | 5' GGTTGGCCCAAAAAAGAAGAGCTCCTGACG 3' | (SEQ ID NO:36) |
| IA-ITS2-121R: | 5' CTTTCAACCACCACTTGTCGTGACGTCCGT 3' | (SEQ ID NO:37) |
| IA-ITS2-151R: | 5' CTCGGTGCCTCACGACATGATGCAAGAGGT 3' | (SEQ ID NO:38) |
| IA-ITS2-181R: | 5' CGCAGGGTCACGATCGGAGCTCGCCGGAGA 3' | (SEQ ID NO:39) |
| IA-ITS2-211R: | 5' GCGGTCGGAGCACCGTCCCGGGAGGAGGTG 3' | (SEQ ID NO:40) |
| IL-ITS2-1F: | 5' CATCACGTCGCCACCAACCCCGATGCCCAG 3' | (SEQ ID NO:41) |
| IL-ITS2-31F: | 5' CTGGATATTAGCGGGAGTTGGGGGCGGAAA 3' | (SEQ ID NO:42) |
| IL-ITS2-61F: | 5' TTGGCCTCCCGTCCACGAACGTGCGCGGTT 3' | (SEQ ID NO:43) |
| IL-ITS2-91F: | 5' GGCCCAAAAAATGAGTTCTTGACGATGGAC 3' | (SEQ ID NO:44) |
| IL-ITS2-121R: | 5' AGAGGTCTTTCAACCACCACTTGCCGTGAC 3' | (SEQ ID NO:45) |
| IL-ITS2-151R: | 5' TACAGACTTGGTGCCTCACGACATGACGCA 3' | (SEQ ID NO:46) |
| IL-ITS2-181R: | 5' AGGGTGCACAGGGTCGCGGTCAGAGCTCGC 3' | (SEQ ID NO:47) |
| IL-ITS2-211R: | 5' GGTCGCGGTCGGAGCACCATCCGTGAAGGA 3' | (SEQ ID NO:48) |
| IR-ITS2-1F: | 5' CATCACGTCGCCCCCAACCCCGACAATGCC 3' | (SEQ ID NO:49) |
| IR-ITS2-31F: | 5' CGGCTGGCAGCCGGATATTGCGGGAGTTGC 3' | (SEQ ID NO:50) |
| IR-ITS2-61F: | 5' GGGCGGAGATTGGCCTCCCGTCCACGACCG 3' | (SEQ ID NO:51) |
| IR-ITS2-91F: | 5' TGCGCGGTTGGCCCAAAAAGCGAGTTCTTG 3' | (SEQ ID NO:52) |
| IR-ITS2-121R: | 5' CCAACCACCACTCGTCGTGACGTCCGTCGT 3' | (SEQ ID NO:53) |
| IR-ITS2-151R: | 5' GGTGCCTCACGACTCGACGCAAGAGGTCTT 3' | (SEQ ID NO:54) |
| IR-ITS2-181R: | 5' GGGTCGCGGTCAGAGCTCGTTACAGACTCG 3' | (SEQ ID NO:55) |
| IR-ITS2-211R: | 5' CGGAGCGCCGCCCCCTAAGGAAGGCGCACA 3' | (SEQ ID NO:56) |

The amplification of ITS fragments using different primer combinations yielded products of various sizes from 60 bp to 240 bp. The relationship between the product size and the primer combination was shown in FIG. 1 and Table 4.

Equal concentrations of PCR fragment products with various sizes of the three *Ilex* species were dotted onto the membrane. Moreover, the entire ITS1 and ITS2 regions of three *Ilex* species were amplified and served as the probes for the dot-blot hybridization analyses. DIG-High Prime (Boehringer Mannheim) was used to label the probes.

Figure 2:
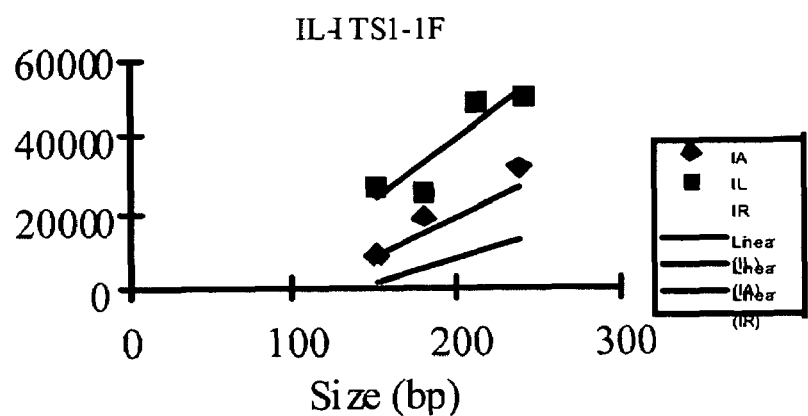
FIG. 2 shows the relationship between signal strength and fragment size of the hybridization of DNA fragments of the ITS1 region of three *Ilex* species to an *Ilex latifolia*-derived probe.
Figure 2:
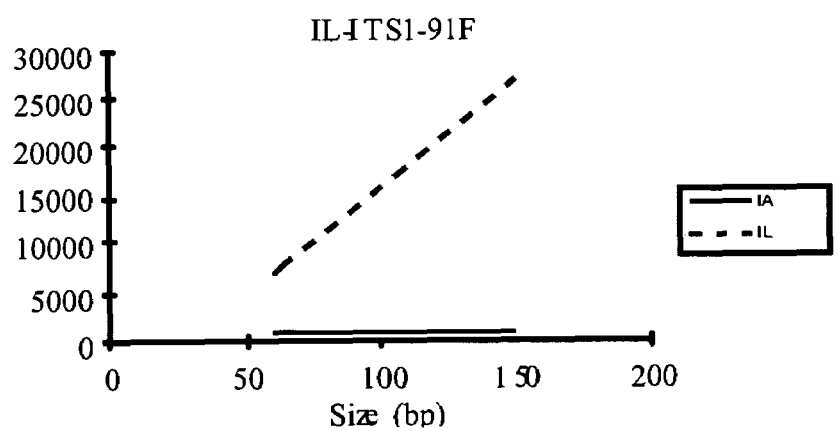
Figure 2:
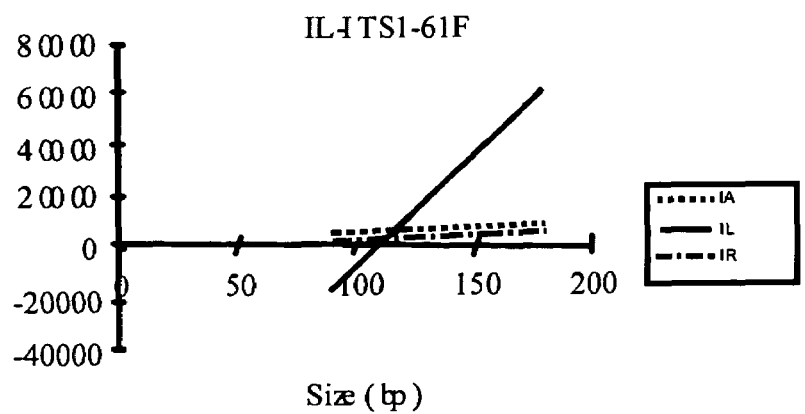
Figure 3:
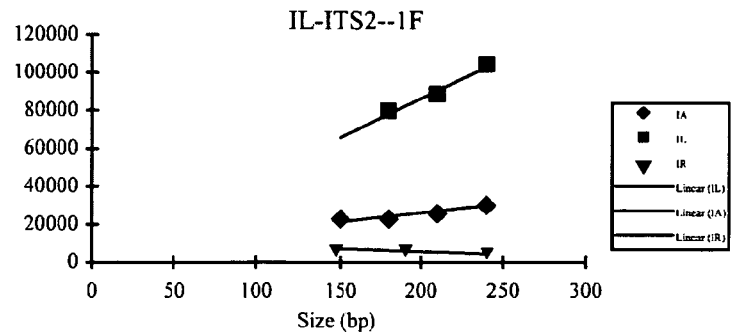
FIG. 3 shows the relationship between signal strength and fragment size of the hybridization of DNA fragments of the ITS2 region of three *Ilex* species to an *Ilex latifolia*-derived probe.
Figure 3:
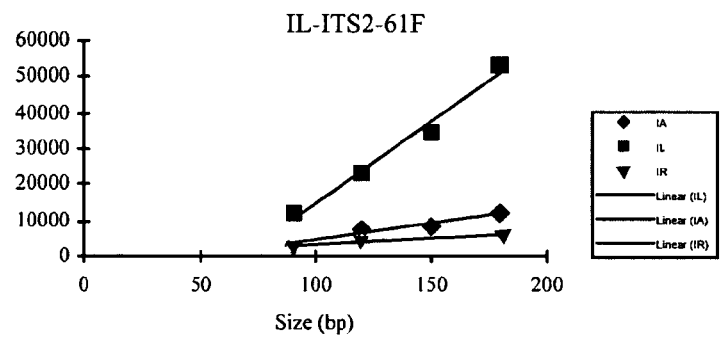
Figure 3:
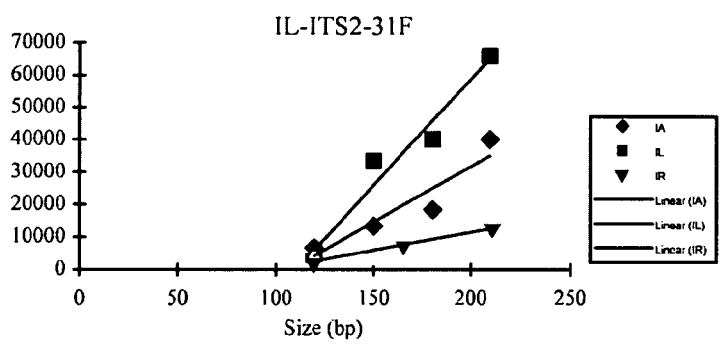
Figure 3:
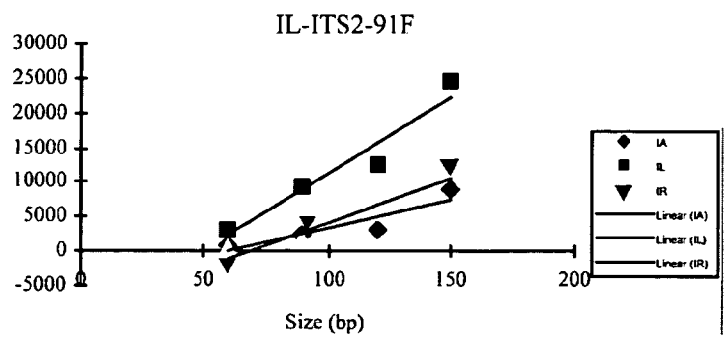

The densities of dots were measured by the Lumi-Analyst software. The measured density of each fragment was plotted against its size, and results obtained with fragments made by amplification with the same forward primer. Only the measurements using *Ilex latifolia* as a probe for hybridization of ITS1 and ITS2 regions were shown in FIGS. 2 and 3. In FIG. 2, primer combinations using the same forward primer to (a) IL-ITS1-1F, (b) IL-ITS1-61F and (c) IL-ITS1-91F were plotted on the same graph; IA=*Ilex asprella*, IL=*Ilex latifolia*, and IR=*Ilex rotunda*. In FIG. 3, primer combinations using the same forward primer of (a) IL-ITS2-1F, (b) IL-ITS2-31F, (c) IL-ITS2-61F and (d) IL-ITS2-91F were plotted on the same graph; IA=*Ilex asprella*, IL=*Ilex latifolia* and IR=*Ilex rotunda*.

The hybridization signal increased with the fragment size. For example, in the case of hybridization of the ITS1 region, when the forward primer IL-ITS1-1F (SEQ ID NO:9) was combined with various reverse primers including IL-ITS1-121R (SEQ ID NO:13), IL-ITS1-151R (SEQ ID NO:14), IL-ITS1-181R (SEQ ID NO:15), and IL-ITS1-211R (SEQ ID NO: 16), the PCR fragment size obtained would be 150 bp, 180 bp, 210 bp and 240 bp respectively. The strength of the hybridization signal increased with the fragment size.

From the plots it was apparent that the hybridization signal of *Ilex latifolia* fragments as compared to hybridization signals of the two other *Ilex* species, was larger as demonstrated by the "height" of the square points in FIGS. 2 and 3. In addition, a linear relationship was observed with *Ilex latifolia* fragments and the *Ilex latifolia* probe. On the other hand, the points obtained from fragments of the other two *Ilex* species were somewhat randomly distributed. Although sometimes a linear relationship could be found for hybridization to fragments of other *Ilex* species, the signal strength of such lines would be much weaker than that of the probing species and the slope of such lines varied from that of the probing species as well. Similarly, this linear relationship was also observed with probes derived from the other species, whether of the ITS1 or the ITS2 region. Therefore, the linear relationship between the signal strength and the fragment size was a useful method for the identification of the plant materials at the species level.

It is apparent from the above results that the presented technique for can be reliably used for identifying biological materials. The means of analysis presented for hybridization of amplified probes of ITS sequences enable reliable authentication of Chinese medicinal materials. The hybridization analysis presented is not dependent on specific restriction enzyme sites found within ITS sequences, and is not sensitive to polymorphisms that alter such restriction enzyme sites. Species of the same genus are easily distinguishable using the approach disclosed herein.

All publications and patent applications mentioned in this specification are herein incorporated by reference to the same extent as if each individual publication or patent application was specifically and individually indicated to be incorporated by reference.

It is understood that the above description and embodiments are intended to illustrate the invention. It is apparent for those skilled in the art to make variations or modifications to the invention or equivalents thereof without departing the spirit of the invention, which should be fallen into the scope of the invention.

The invention claimed is:

1. A method for preparing an array for authenticating whether a plant sample is originated from a known plant, the method comprising the steps of:
   a) extracting DNA from the known plant;
   b) amplifying variable regions from the extracted DNA to obtain nucleotide sequences of the variable region;
   c) designing specific primers containing one forward primer and a plurality of reverse primers according to the nucleotide sequences;
   d) amplifying the variable region by separated PCRs with combinations of the specific primers to obtain DNA fragments having different sizes; and
   e) dotting the DNA fragments onto a solid support.

2. The method of claim 1, wherein the variable region include ITSs, ETSs or IGRs.

3. The method of claim 2, wherein the variable region is ITS1 or ITS2.

4. The method of claim 3, wherein the known plant is *Ilex asprella, Ilex latifolia* or *Ilex rotunda*.

5. The method of claim 4, wherein the specific primers comprise nucleotide sequences selected from the group consisting of: SEQ ID NO: 9, SEQ ID NO: 10, SEQ ID NO:11, SEQ ID NO: 12, SEQ ID NO: 13, SEQ ID NO: 14, SEQ ID NO: 15, SEQ ID NO: 16, SEQ ID NO:17, SEQ ID NO: 18, SEQ ID NO:19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO:45, SEQ ID NO: 46, SEQ ID NO: 47, SEQ ID NO: 48, SEQ ID NO: 49, SEQ ID NO: 50, SEQ ID NO: 51, SEQ ID NO:52, SEQ ID NO: 53, SEQ ID NO: 54, SEQ ID NO:55, and SEQ ID NO:56.

6. The method of claim 4, wherein the step b) further comprises:
   amplifying the ITS1 region using primers IL-ITS1-143 (SEQ ID NO:7) and IL-ITS1-499R (SEQ ID NO:8) to reduce rRNA 18S and 5.8S regions flanking the ITS1 region of the nucleotide sequences.

7. The method of claim 3, wherein the ITS1 region comprises a sequence selected from the group consisting of SEQ ID NO:1, SEQ ID NO:2 and SEQ ID NO:3.

8. The method of claim 4, wherein the ITS1 region comprises a sequence selected from the group consisting of SEQ ID NO:1, SEQ ID NO:2 and SEQ ID NO:3.

9. The method of claim 5, wherein the ITS1 region comprises a sequence selected from the group consisting of SEQ ID NO:1, SEQ ID NO:2 and SEQ ID NO:3.

10. The method of claim 3, wherein the ITS2 region comprises a sequence selected from the group consisting of: SEQ ID NO:4, SEQ ID NO:5 and SEQ ID NO:6.

11. The method of claim 4, wherein the ITS2 region comprises a sequence selected from the group consisting of: SEQ ID NO:4, SEQ ID NO:5 and SEQ ID NO:6.

12. The method of claim 5, wherein the ITS2 region comprises a sequence selected from the group consisting of: SEQ ID NO:4, SEQ ID NO:5 and SEQ ID NO:6.

13. The method of claim 7, wherein the ITS2 region comprises a sequence selected from the group consisting of: SEQ ID NO:4, SEQ ID NO:5 and SEQ ID NO:6.

14. The method of claim 8, wherein the ITS2 region comprises a sequence selected from the group consisting of: SEQ ID NO:4, SEQ ID NO:5 and SEQ ID NO:6.

15. The method of claim 9, wherein the ITS2 region comprises a sequence selected from the group consisting of: SEQ ID NO:4, SEQ ID NO:5 and SEQ ID NO:6.

16. A method for determining whether a plant sample is originated from a known plant, wherein the method comprises:
   a) extracting first DNAs from the known plant;
   b) amplifying variable regions from the extracted first DNAs to obtain a nucleotide sequences of the variable regions;
   c) designing specific primers comprising one forward primer and a plurality of reverse primers according to the nucleotide sequence;
   d) amplifying the variable regions by separated PCRs with the combinations of the specific primers to obtain DNA fragments having different sizes;
   e) dotting the DNA fragments onto a solid support to obtain an array;
   f) extracting second DNAs and third DNAs from the plant sample and the known plant, respectively;
   g) respectively amplifying the variable regions from the extracted second and third DNAs to produce sample probes and control probes which are derived from the known plant;
   h) hybridizing the sample and control probes with the array, respectively to obtain corresponding hybridization signals; and
   i) processing the hybridization signals, whether the hybridization signal increasing with the fragment size in a linear relationship indicates the plant sample is originated from the known plant.

17. The method of claim 16, wherein the variable region include ITSs, ETSs or IGRs.

18. The method of claim 17, wherein the variable region is ITS1 or ITS2.

19. The method of claim 18, wherein the known plant is *Ilex asprella, Ilex latifolia* or *Ilex rotunda*.

20. The method of claim 19, wherein the specific primers comprise nucleotide sequences selected from the group consisting of: SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO:17, SEQ ID NO: 18, SEQ ID NO:19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO:45, SEQ ID NO: 46, SEQ ID NO: 47, SEQ ID NO: 48, SEQ ID NO: 49, SEQ ID NO: 50, SEQ ID NO: 51, SEQ ID NO:52, SEQ ID NO: 53, SEQ ID NO: 54, SEQ ID NO:55, and SEQ ID NO:56.

21. The method of claim 18, wherein the steps b) and g) further comprises: amplifying the ITS1 region using primers IL-ITS1-143 (SEQ ID NO:7) and IL-ITS1-499R (SEQ ID NO:8) to reduce rRNA 18S and 5.8S regions flanking the ITS1 region of the nucleotide sequences.

22. The method of claim 16, wherein the step i) comprises comparing the hybridization values of the sample probes to those of the control probes to see whether both of them are identical.

23. The method of claim 16, wherein the step i) comprises plotting a graph of the length of the fragments versus corresponding values of the hybridization signals, and linearly regressing the graph.

24. The method of claim 16, wherein the probes are labeled with a detectable moiety.

25. The method of claim 24, wherein the detectable moiety is dioxigenin.

26. The method of claim 19, wherein the control probes comprise a sequence selected from the group comprising of: SEQ IN NO:1, SEQ IN NO:2, SEQ IN NO:3, SEQ IN NO:4, SEQ IN NO:5 and SEQ IN NO:6.

27. The method of claim 18, wherein the ITS1 region comprises a sequence selected from the group consisting of SEQ ID NO:1, SEQ ID NO:2 and SEQ ID NO:3.

28. The method of claim 18, wherein the ITS2 region comprises a sequence selected from the group consisting of: SEQ ID NO:4, SEQ ID NO:5 and SEQ ID NO:6.

* * * * *

SEQUENCE LISTING

<160> NUMBER OF SEQ ID NOS: 60

<210> SEQ ID NO 1
<211> LENGTH: 243
<212> TYPE: DNA
<213> ORGANISM: Ilex asprella

<400> SEQUENCE: 1

```
cgatgcctgc aaagtagacc cggcgaacct gttaaaatat gcttgggggt ctgagaaggg      60
gtgcgcgagc cccccgacac actcccctac ctcgggattt ggcttgcgtt ccccagcgg     120 ggactcggcc aagctcccga caacgaaccc cggcgctgtc tgcgccaagg aaccttaacc     180
gaagagctgg cccccgatg tcccgttcgc ggtgtgcacg ggaagcatac gcgtcttttg     240
aat                                                                    243
```

<210> SEQ ID NO 2
<211> LENGTH: 248
<212> TYPE: DNA
<213> ORGANISM: Ilex latifolia

<400> SEQUENCE: 2

```
cgatgcctgc aaagtagacc cggcgaactt gttaaaatat gcctgggggt ttgagaaggg      60
gtgcgcgagc cccccgacac actcccccag cccctcggg atttggcttg cgttcccta     120 gcggggactc ggtcaagctc ccgacaacga accccggcgc tatctgcgcc aaggaaccat     180
aactgaaggg ctggcctccc gatgtcccgt tcgcggcgtg caacgggagg catctgcatc     240
ttttgaat                                                                248
```

<210> SEQ ID NO 3

```
<211> LENGTH: 250
<212> TYPE: DNA
<213> ORGANISM: Ilex rotunda

<400> SEQUENCE: 3
cgatgcctgc aaagtagacc cggcgaactc gttaaaatat gcgtgggggt ttgagaaggg    60
gcgcgcgagc cccctcgac acaattcccc cacccccgg gacttggccc gggttcccct     120 tgcgggact cggccaaggc tcccgacaac gaaccccggc gctgtctgcg ccaaggaacc    180
cttaaccgaa gagctggccc cccggtgtcc cgttcgcggt gtgcacgggg ggcgtacgca    240
tctttcgaat                                                          250

<210> SEQ ID NO 4
<211> LENGTH: 238
<212> TYPE: DNA
<213> ORGANISM: Ilex asprella

<400> SEQUENCE: 4
catcccgtcg ccccccaacc ccaatgccta gctagctgga tattgcggga gttgggggcg    60
gaaattggcc tcccgtccac gaccgtgcgc ggttggccca aaaagaaga gctcctgacg    120 acggacgtca cgacaagtgg tggttgaaag acctcttgca tcatgtcgtg aggcaccgag    180
tctccggcga gctccgatcg tgaccctgcg cacctcctcc cgggacggtg ctccgacc     238

<210> SEQ ID NO 5
<211> LENGTH: 234
<212> TYPE: DNA
<213> ORGANISM: Ilex latifolia

<400> SEQUENCE: 5
catcacgtcg ccaccaaccc cgatgcccag ctggatatta gcgggagttg ggggcggaaa    60
ttggcctccc gtccacgaac gtgcgcggtt ggcccaaaaa atgagttctt gacgatggac    120
gtcacggcaa gtggtggttg aaagacctct tgcgtcatgt cgtgaggcac caagtctgta    180
gcgagctctg accgcgaccc tgtgcaccct tccttcacgg atggtgctcc gacc         234

<210> SEQ ID NO 6
<211> LENGTH: 242
<212> TYPE: DNA
<213> ORGANISM: Ilex rotunda

<400> SEQUENCE: 6
catcacgtcg ccccccaaccc cgacaatgcc cggctggcag ccggatattg cgggagttgc    60
gggcggagat tggcctcccg tccacgaccg tgcgcggttg gcccaaaaag cgagttcttg    120
acgacggacg tcacgacgag tggtggttgg aagacctctt gcgtcgagtc gtgaggcacc    180
cgagtctgta acgagctctg accgcgaccc tgtgcgcctt ccttaggggg cggcgctccg    240
ac                                                                  242

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gaacctgcgg aaggatcatt                                               20
```

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
cgagagccga gatatccgtt                                           20

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
cgatgcctgc aaagtagacc cggcgaacct                                30

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
gttaaaatat gcctgggggt ttgagaaggg                                30

<210> SEQ ID NO 11
<211> LENGTH: 30
<212> TYPE: DNA
<213> ORGANISM: Artificial Sequence
<220> FEATURE:
<223> OTHER INFORMATION: Primer

<400> SEQUENCE: 11
gtgcgcgagc ccccccgacac actcccctac                               30

<210> SEQ ID NO 12
<211> LENGTH: 30
<212> TYPE: DNA
<213> ORGANISM: Artificial Sequence
<220> FEATURE:
<223> OTHER INFORMATION: Primer

<400> SEQUENCE: 12
ctcgggattt ggcttgcgtt cccccagcgg                                30

<210> SEQ ID NO 13
<211> LENGTH: 30
<212> TYPE: DNA
<213> ORGANISM: Artificial Sequence
<220> FEATURE:
<223> OTHER INFORMATION: Primer

<400> SEQUENCE: 13
gggttcgttg tcgggagctt ggccgagtcc                                30

<210> SEQ ID NO 14
<211> LENGTH: 30
<212> TYPE: DNA
<213> ORGANISM: Artificial Sequence
<220> FEATURE:
<223> OTHER INFORMATION: Primer

```
<400> SEQUENCE: 14
ggttaaggtt ccttggcgca gacagcgccg                              30

<210> SEQ ID NO 15
<211> LENGTH: 30
<212> TYPE: DNA
<213> ORGANISM: Artificial Sequence
<220> FEATURE:
<223> OTHER INFORMATION: Primer

<400> SEQUENCE: 15
gcgaacggga catcgggggg ccagctcttc                              30

<210> SEQ ID NO 16
<211> LENGTH: 30
<212> TYPE: DNA
<213> ORGANISM: Artificial Sequence
<220> FEATURE:
<223> OTHER INFORMATION: Primer

<400> SEQUENCE: 16
aaaagacgcg tatgcttccc gttgcacacc                              30

<210> SEQ ID NO 17
<211> LENGTH: 30
<212> TYPE: DNA
<213> ORGANISM: Artificial Sequence
<220> FEATURE:
<223> OTHER INFORMATION: Primer

<400> SEQUENCE: 17
cgatgcctgc aaagtagacc cggcgaactt                              30

<210> SEQ ID NO 18
<211> LENGTH: 30
<212> TYPE: DNA
<213> ORGANISM: Artificial Sequence
<220> FEATURE:
<223> OTHER INFORMATION: Primer

<400> SEQUENCE: 18
gttaaaatat gcctgggggt ttgagaaggg                              30

<210> SEQ ID NO 19
<211> LENGTH: 30
<212> TYPE: DNA
<213> ORGANISM: Artificial Sequence
<220> FEATURE:
<223> OTHER INFORMATION: Primer

<400> SEQUENCE: 19
gtgcgcgagc ccccgacac actcccccag                               30

<210> SEQ ID NO 20
<211> LENGTH: 30
<212> TYPE: DNA
<213> ORGANISM: Artificial Sequence
<220> FEATURE:
<223> OTHER INFORMATION: Primer

<400> SEQUENCE: 20 cccctcggg atttggcttg cgttcccta                                30

<210> SEQ ID NO 21
<211> LENGTH: 30
```

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
tcgttgtcgg gagcttgacc gagtccccgc          30

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
atggttcctt ggcgcagata gcgccggggt          30

<210> SEQ ID NO 23
<211> LENGTH: 30
<212> TYPE: DNA
<213> ORGANISM: Artificial Sequence
<220> FEATURE:
<223> OTHER INFORMATION: Primer

<400> SEQUENCE: 23
acgggacatc gggaggccag cccttcagtt          30

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
gatgcagatg cctcccgttg cacgccgcga          30

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
cgatgcctgc aaagtagacc cggcgaactc          30

<210> SEQ ID NO 26
<211> LENGTH: 30
<212> TYPE: DNA
<213> ORGANISM: Artificial Sequence
<220> FEATURE:
<223> OTHER INFORMATION: Primer

<400> SEQUENCE: 26
gttaaaatat gcgtgggggt ttgagaaggg          30

<210> SEQ ID NO 27
<211> LENGTH: 30
<212> TYPE: DNA
<213> ORGANISM: Artificial Sequence
<220> FEATURE:
<223> OTHER INFORMATION: Primer

<400> SEQUENCE: 27
gcgcgcgagc cccctcgac acactccccc                        30

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
acccccgggg acttggcccg ggttcccctt                        30

<210> SEQ ID NO 29
<211> LENGTH: 30
<212> TYPE: DNA
<213> ORGANISM: Artificial Sequence
<220> FEATURE:
<223> OTHER INFORMATION: Primer

<400> SEQUENCE: 29
cgttgtcggg agccttggcc gagtccccgc                        30

<210> SEQ ID NO 30
<211> LENGTH: 30
<212> TYPE: DNA
<213> ORGANISM: Artificial Sequence
<220> FEATURE:
<223> OTHER INFORMATION: Primer

<400> SEQUENCE: 30
gggttccttg gcgcagacag cgccggggtt                        30

<210> SEQ ID NO 31
<211> LENGTH: 30
<212> TYPE: DNA
<213> ORGANISM: Artificial Sequence
<220> FEATURE:
<223> OTHER INFORMATION: Primer

<400> SEQUENCE: 31
gggacaccgg ggggccagct cttcggttaa                        30

<210> SEQ ID NO 32
<211> LENGTH: 30
<212> TYPE: DNA
<213> ORGANISM: Artificial Sequence
<220> FEATURE:
<223> OTHER INFORMATION: Primer

<400> SEQUENCE: 32
atgcgtacgc ctcccgtgca caccgcgaac                        30

<210> SEQ ID NO 33
<211> LENGTH: 30
<212> TYPE: DNA
<213> ORGANISM: Artificial Sequence
<220> FEATURE:
<223> OTHER INFORMATION: Primer

<400> SEQUENCE: 33
catcccgtcg cccccaacc ccaatgccta                         30

<210> SEQ ID NO 34
<211> LENGTH: 30
<212> TYPE: DNA
<213> ORGANISM: Artificial Sequence

```
<220> FEATURE:
<223> OTHER INFORMATION: Primer

<400> SEQUENCE: 34
gctagctgga tattgcggga gttgggggcg                                30

<210> SEQ ID NO 35
<211> LENGTH: 30
<212> TYPE: DNA
<213> ORGANISM: Artificial Sequence
<220> FEATURE:
<223> OTHER INFORMATION: Primer

<400> SEQUENCE: 35
gaaattggcc tcccgtccac gaccgtgcgc                                30

<210> SEQ ID NO 36
<211> LENGTH: 30
<212> TYPE: DNA
<213> ORGANISM: Artificial Sequence
<220> FEATURE:
<223> OTHER INFORMATION: Primer

<400> SEQUENCE: 36
ggttggccca aaaagaaga gctcctgacg                                 30

<210> SEQ ID NO 37
<211> LENGTH: 30
<212> TYPE: DNA
<213> ORGANISM: Artificial Sequence
<220> FEATURE:
<223> OTHER INFORMATION: Primer

<400> SEQUENCE: 37
ctttcaacca ccacttgtcg tgacgtccgt                                30

<210> SEQ ID NO 38
<211> LENGTH: 30
<212> TYPE: DNA
<213> ORGANISM: Artificial Sequence
<220> FEATURE:
<223> OTHER INFORMATION: Primer

<400> SEQUENCE: 38
ctcggtgcct cacgacatga tgcaagaggt                                30

<210> SEQ ID NO 39
<211> LENGTH: 30
<212> TYPE: DNA
<213> ORGANISM: Artificial Sequence
<220> FEATURE:
<223> OTHER INFORMATION: Primer

<400> SEQUENCE: 39
cgcagggtca cgatcggagc tcgccggaga                                30

<210> SEQ ID NO 40
<211> LENGTH: 30
<212> TYPE: DNA
<213> ORGANISM: Artificial Sequence
<220> FEATURE:
<223> OTHER INFORMATION: Primer

<400> SEQUENCE: 40
gcggtcggag caccgtcccg ggaggaggtg                                30
```

<210> SEQ ID NO 41
<211> LENGTH: 30
<212> TYPE: DNA
<213> ORGANISM: Artificial Sequence
<220> FEATURE:
<223> OTHER INFORMATION: Primer

<400> SEQUENCE: 41
catcacgtcg ccaccaaccc cgatgcccag                                    30

<210> SEQ ID NO 42
<211> LENGTH: 30
<212> TYPE: DNA
<213> ORGANISM: Artificial Sequence
<220> FEATURE:
<223> OTHER INFORMATION: Primer

<400> SEQUENCE: 42
ctggatatta gcgggagttg ggggcggaaa                                    30

<210> SEQ ID NO 43
<211> LENGTH: 30
<212> TYPE: DNA
<213> ORGANISM: Artificial Sequence
<220> FEATURE:
<223> OTHER INFORMATION: Primer

<400> SEQUENCE: 43
ttggcctccc gtccacgaac gtgcgcggtt                                    30

<210> SEQ ID NO 44
<211> LENGTH: 30
<212> TYPE: DNA
<213> ORGANISM: Artificial Sequence
<220> FEATURE:
<223> OTHER INFORMATION: Primer

<400> SEQUENCE: 44
ggcccaaaaa atgagttctt gacgatggac                                    30

<210> SEQ ID NO 45
<211> LENGTH: 30
<212> TYPE: DNA
<213> ORGANISM: Artificial Sequence
<220> FEATURE:
<223> OTHER INFORMATION: Primer

<400> SEQUENCE: 45
agaggtcttt caaccaccac ttgccgtgac                                    30

<210> SEQ ID NO 46
<211> LENGTH: 30
<212> TYPE: DNA
<213> ORGANISM: Artificial Sequence
<220> FEATURE:
<223> OTHER INFORMATION: Primer

<400> SEQUENCE: 46
tacagacttg gtgcctcacg acatgacgca                                    30

<210> SEQ ID NO 47
<211> LENGTH: 30
<212> TYPE: DNA
<213> ORGANISM: Artificial Sequence
<220> FEATURE:
<223> OTHER INFORMATION: Primer

```
<400> SEQUENCE: 47
agggtgcaca gggtcgcggt cagagctcgc                                    30

<210> SEQ ID NO 48
<211> LENGTH: 30
<212> TYPE: DNA
<213> ORGANISM: Artificial Sequence
<220> FEATURE:
<223> OTHER INFORMATION: Primer

<400> SEQUENCE: 48
ggtcgcggtc ggagcaccat ccgtgaagga                                    30

<210> SEQ ID NO 49
<211> LENGTH: 30
<212> TYPE: DNA
<213> ORGANISM: Artificial Sequence
<220> FEATURE:
<223> OTHER INFORMATION: Primer

<400> SEQUENCE: 49
catcacgtcg cccccaaccc cgacaatgcc                                    30

<210> SEQ ID NO 50
<211> LENGTH: 30
<212> TYPE: DNA
<213> ORGANISM: Artificial Sequence
<220> FEATURE:
<223> OTHER INFORMATION: Primer

<400> SEQUENCE: 50
cggctggcag ccggatattg cgggagttgc                                    30

<210> SEQ ID NO 51
<211> LENGTH: 30
<212> TYPE: DNA
<213> ORGANISM: Artificial Sequence
<220> FEATURE:
<223> OTHER INFORMATION: Primer

<400> SEQUENCE: 51
gggcggagat tggcctcccg tccacgaccg                                    30

<210> SEQ ID NO 52
<211> LENGTH: 30
<212> TYPE: DNA
<213> ORGANISM: Artificial Sequence
<220> FEATURE:
<223> OTHER INFORMATION: Primer

<400> SEQUENCE: 52
tgcgcggttg gcccaaaaag cgagttcttg                                    30

<210> SEQ ID NO 53
<211> LENGTH: 30
<212> TYPE: DNA
<213> ORGANISM: Artificial Sequence
<220> FEATURE:
<223> OTHER INFORMATION: Primer

<400> SEQUENCE: 53
ccaaccacca ctcgtcgtga cgtccgtcgt                                    30

<210> SEQ ID NO 54
```

```
<211> LENGTH: 30
<212> TYPE: DNA
<213> ORGANISM: Artificial Sequence
<220> FEATURE:
<223> OTHER INFORMATION: Primer

<400> SEQUENCE: 54
ggtgcctcac gactcgacgc aagaggtctt                                              30

<210> SEQ ID NO 55
<211> LENGTH: 30
<212> TYPE: DNA
<213> ORGANISM: Artificial Sequence
<220> FEATURE:
<223> OTHER INFORMATION: Primer

<400> SEQUENCE: 55
gggtcgcggt cagagctcgt tacagactcg                                              30

<210> SEQ ID NO 56
<211> LENGTH: 30
<212> TYPE: DNA
<213> ORGANISM: Artificial Sequence
<220> FEATURE:
<223> OTHER INFORMATION: Primer

<400> SEQUENCE: 56
cggagcgccg cccctaagg aaggcgcaca                                               30

<210> SEQ ID NO 57
<211> LENGTH: 31
<212> TYPE: DNA
<213> ORGANISM: Artificial Sequence
<220> FEATURE:
<223> OTHER INFORMATION: Primer

<400> SEQUENCE: 57
aggaatgcct agtaagcgcg agtcatcagc t                                            31

<210> SEQ ID NO 58
<211> LENGTH: 25
<212> TYPE: DNA
<213> ORGANISM: Artificial Sequence
<220> FEATURE:
<223> OTHER INFORMATION: Primer

<400> SEQUENCE: 58
ttgcgttcaa agactcgatg gttca                                                   25

<210> SEQ ID NO 59
<211> LENGTH: 25
<212> TYPE: DNA
<213> ORGANISM: Artificial Sequence
<220> FEATURE:
<223> OTHER INFORMATION: Primer

<400> SEQUENCE: 59
tgaaccatcg agtctttgaa cgcaa                                                   25

<210> SEQ ID NO 60
<211> LENGTH: 30
<212> TYPE: DNA
<213> ORGANISM: Artificial Sequence
```

```
<220> FEATURE:
<223> OTHER INFORMATION: Primer

<400> SEQUENCE: 60
actcgccgtt actagggaa tcctcgtaag                                30
```